(12) United States Patent
Hintz et al.

(10) Patent No.: US 8,916,004 B2
(45) Date of Patent: Dec. 23, 2014

(54) THERMAL NITRIDING PROCESS FOR COMPONENTS OF IMPLANTABLE MEDICAL DEVICES

(75) Inventors: Michael B. Hintz, Mahtomedi, MN (US); Peter D. Yurek, North St. Paul, MN (US); Brad C. Tischendorf, Minneapolis, MN (US); William J. Taylor, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 792 days.

(21) Appl. No.: 13/172,072

(22) Filed: Jun. 29, 2011

(65) Prior Publication Data
US 2013/0006320 A1    Jan. 3, 2013

(51) Int. Cl.
*C23C 8/24*        (2006.01)
*A61N 1/00*        (2006.01)
*H01M 4/66*        (2006.01)
*A61N 1/378*       (2006.01)
*A61N 1/375*       (2006.01)

(52) U.S. Cl.
CPC . *A61N 1/378* (2013.01); *C23C 8/24* (2013.01); *A61N 1/375* (2013.01)
USPC ............... 148/237; 148/223; 148/317; 607/5; 607/2; 607/36; 429/519

(58) Field of Classification Search
USPC .................... 148/237, 223, 317; 607/5, 2, 36; 429/519
See application file for complete search history.

(56) References Cited

U.S. PATENT DOCUMENTS

| 4,768,757 | A  | * | 9/1988  | Nakamura et al. ............. 266/252 |
| 5,464,706 | A  |   | 11/1995 | Dasgupta et al. |
| 7,083,877 | B2 |   | 8/2006  | Iwamoto et al. |
| 2004/0048157 | A1 | | 3/2004  | Neudecker et al. |
| 2007/0202395 | A1 | | 8/2007  | Snyder et al. |

OTHER PUBLICATIONS

Zhecheva, Ani, et al. "Enhancing the microstructure and properties of titanium alloys through nitriding and other surface engineering methods." Surface and Coatings Technology 200.7 (2005): 2192-2207.*

* cited by examiner

*Primary Examiner* — Jessee Roe

(57) ABSTRACT

A component of an implantable medical device comprises a body comprising at least one external surface, the body comprising at least one of titanium, titanium-based alloys, and composites thereof, and a corrosion-resistant surface region at the at least one external surface, the corrosion-resistant surface region comprising at least one of titanium nitride, dititanium nitride, and a solid solution of nitrogen dissolved in the body, wherein the corrosion-resistant surface region is formed by thermal nitridation of the body.

19 Claims, 12 Drawing Sheets

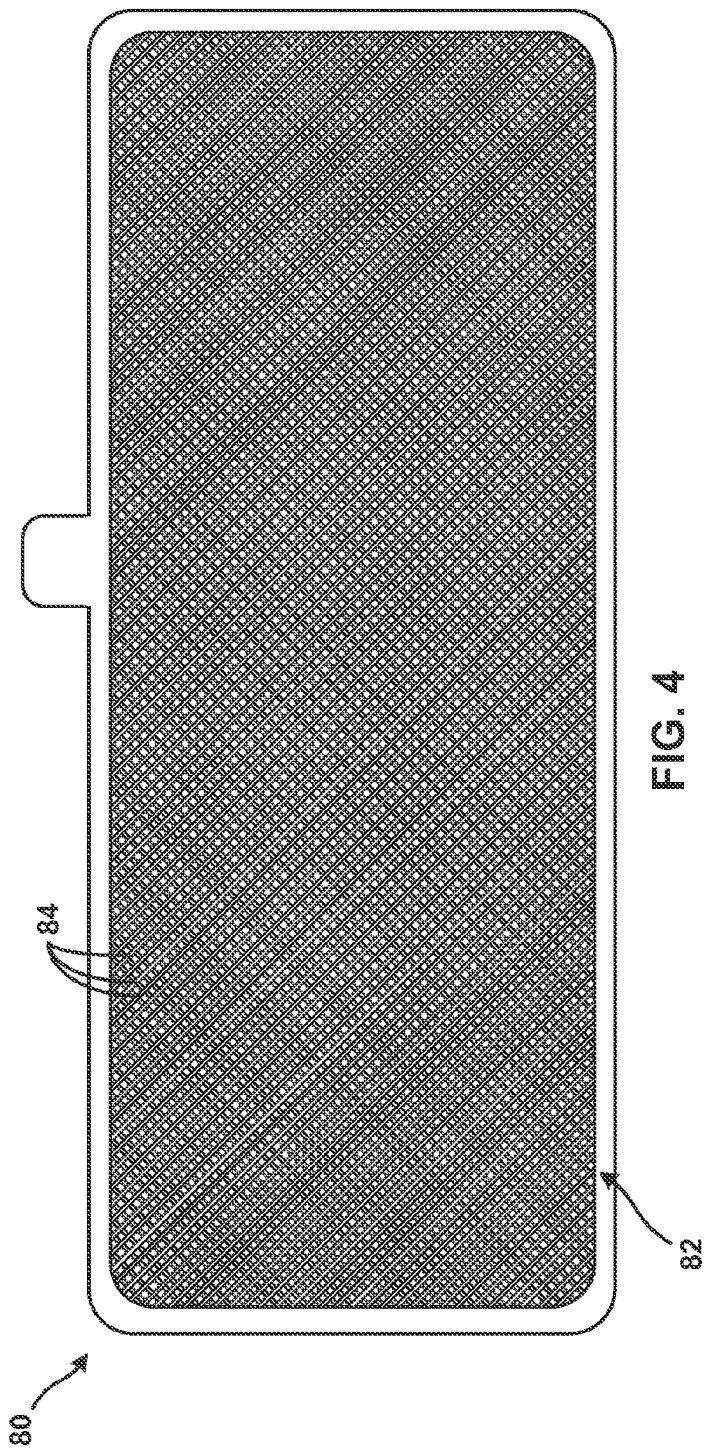
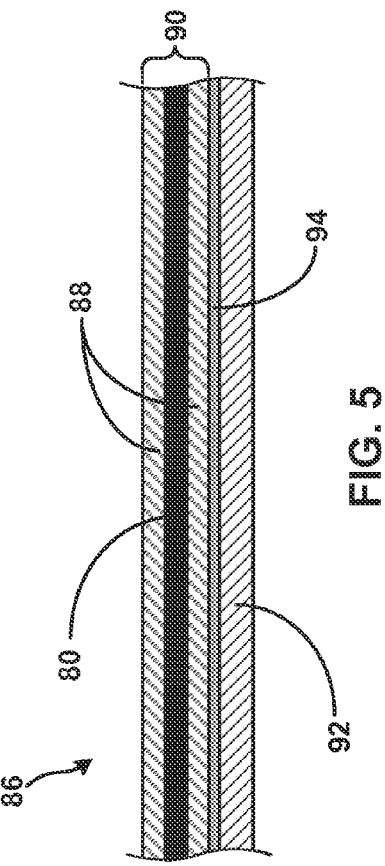

us 8,916,004 B2

THERMAL NITRIDING PROCESS FOR COMPONENTS OF IMPLANTABLE MEDICAL DEVICES

TECHNICAL FIELD

The invention relates to a process for coating titanium components to protect against corrosion, such as titanium components within batteries of implantable medical devices.

BACKGROUND

Titanium is often used in implantable medical devices because it is biocompatible. Although titanium is generally stable in implantable medical devices, it is sometimes desired to use titanium in aggressive chemical environments, for example as components within an electrical power source of the implantable medical device, such as within an electrochemical cell, also referred to herein as a cell or a battery. In some cases, the electrolyte compounds used to create an electrochemical cell can be corrosive to titanium components. For example, a fluorine-containing electrolyte may corrode a titanium current collector that is used to mechanically support and provide electrical contact to a battery cathode. The fluorine may react with the titanium to form compounds comprising fluorine and titanium that are electrically insulating so that electrical contact between the current collector and the cathode material may become degraded. Over time, as more and more of the titanium is corroded, the overall electrical impedance of the battery increases over the life of the battery so that the battery provides less power over time to the implantable medical device.

SUMMARY

In general, the present disclosure is directed to methods of providing a nitrogen-enriched coating on titanium components of implantable medical devices and medical devices made therefrom. The method comprises using a thermal nitriding process to grow a corrosion-resistant surface region of increased nitrogen concentration on a titanium component. The corrosion-resistant surface region produced by the method of the present disclosure provides for corrosion protection of titanium components that are present in aggressive chemical environments, such as within a battery of the implantable medical device.

In one example, the disclosure is directed to a component of an implantable medical device, the component comprising a body comprising at least one external surface, the body comprising at least one of titanium, titanium-based alloys, and composites thereof, and a corrosion-resistant surface region at the at least one external surface, the corrosion-resistant surface region comprising at least one of titanium nitride, dititanium nitride, and a solid solution of nitrogen dissolved in the body, wherein the corrosion-resistant surface region is formed by thermal nitridation of the body.

In another example, the disclosure is directed to a method comprising baking a component of an implantable medical device, the component comprising at least one of titanium, a titanium-based alloy, or composites thereof, and simultaneously exposing the component to a nitrogen-bearing gas so that a corrosion-resistant surface region forms at an exposed surface of the component, the corrosion-resistant surface region comprising at least one of titanium nitride, dititanium nitride, and a solid solution of nitrogen dissolved in the component.

In another example, the present disclosure is directed to an implantable medical device comprising electronics configured to deliver a therapy to a target tissue via a lead or to sense bioelectric signals proximate the target tissue via the lead, a battery electrically coupled to the electronics, the battery comprising an electrochemical cell comprising an electrolyte, a current collector comprising at least one surface exposed to the electrolyte, the current collector comprising at least one of titanium, a titanium-based alloy, and composites thereof, and a corrosion-resistant surface region formed at the at least one exposed surface, the corrosion-resistant surface region comprising at least one of titanium nitride, dititanium nitride, and a solid solution of nitrogen dissolved in the current collector, wherein the corrosion-resistant surface region is formed by thermal nitridation of the current collector.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 4 is a view showing an example current collector that may be used as part of the cathode of the battery of FIG. 3.

FIG. 5 is a cross-sectional view showing a battery electrode assembly comprising the example current collector of FIG. 4.

DETAILED DESCRIPTION

Figure 1:
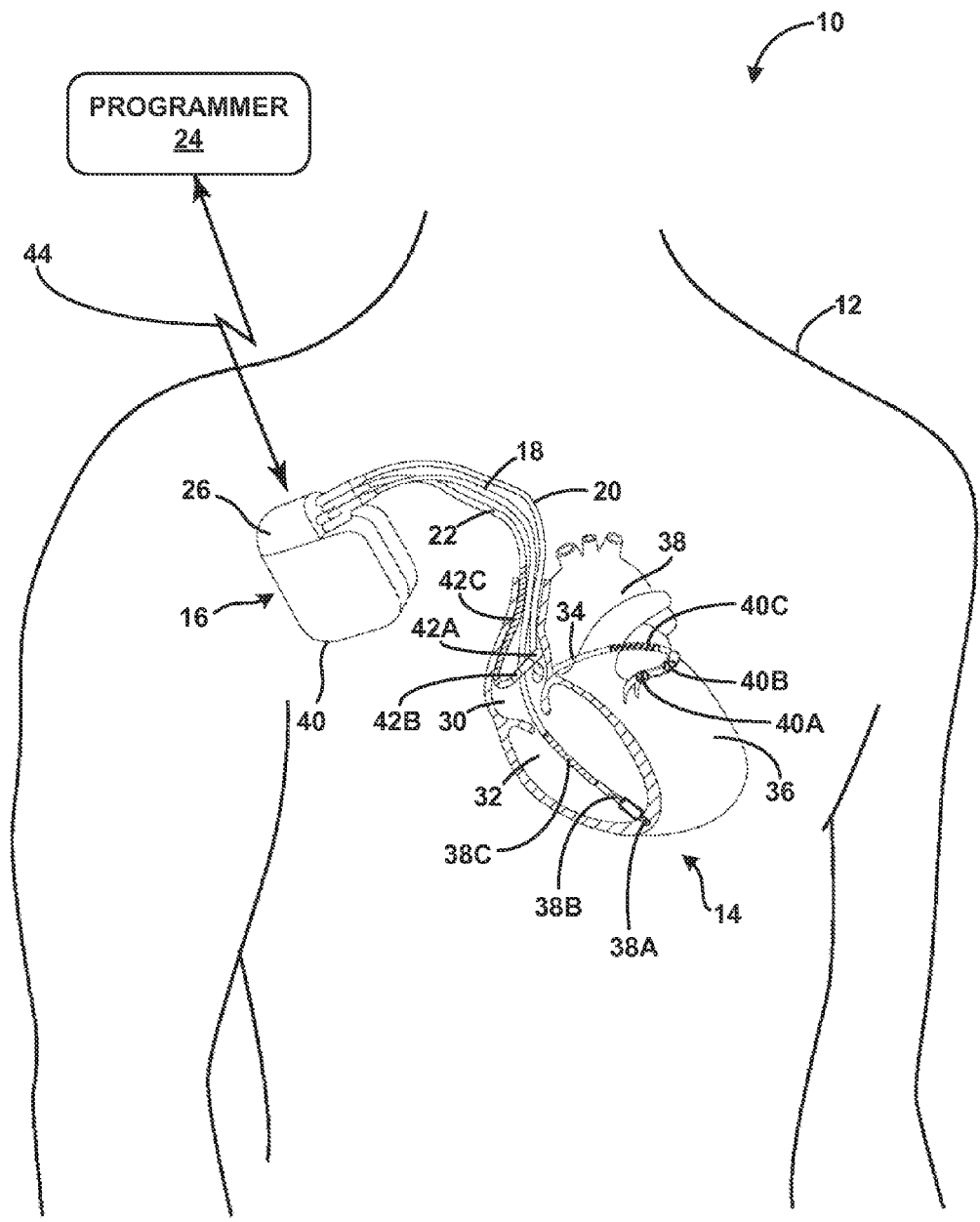
FIG. 1 is a conceptual diagram illustrating an example therapy system comprising an implantable medical device for the delivery of cardiac stimulation therapy to a patient.

In general, the present disclosure is directed to methods of providing a corrosion-resistant coating on titanium or titanium-based alloy components used in implantable medical devices that may be exposed to aggressive chemical environments (also referred to herein as "corrosive environments"), such as within a battery of the implantable medical device. The method comprises using a thermal nitriding process to form a thin corrosion-resistant surface region or film at or proximate to an exposed surface of the titanium or titanium-based alloy component. The corrosion-resistant surface region may comprise an increased nitrogen concentration at or proximate to the exposed surface, wherein the surface region of increased nitrogen concentration may comprise at least one of titanium nitride (TiN), dititanium nitride ($Ti_2N$), or a solid solution of nitrogen dissolved into the bulk of the titanium or titanium-based alloy component. The corrosion-resistant surface region may comprise a region at or proximate the exposed surface that exhibits elevated nitrogen content due to the thermal nitriding process described in more detail below. The thermal nitriding process described in the present disclosure allows for the formation of a thin, strongly-adhered corrosion-resistant surface region or film onto a titanium or titanium-based alloy component.

Titanium and titanium-based alloys are used in many components of implantable medical devices (IMDs) because they are biocompatible and generally exhibit good corrosion resistance in many chemical environments. As used herein, the term "titanium-based alloy" may refer to an alloy comprising at least about 75% titanium by weight, such as at least about 85%, titanium by weight, for example at least about 90% titanium by weight, such as at least about 95% titanium by weight. Examples of components that may comprise titanium or a titanium-based alloy include an external housing of the IMD and components of a battery of the IMD, for a battery housing and internal battery components such as a cathode current collector. In some examples, a battery cathode may comprise materials which exist in finely divided forms such as powders or small fibers. A cathode current collector may function to mechanically support the finely divided cathode material or materials and to enable reliable electrical contact to the finely divided cathode material or materials. A composite cathode assembly may be formed by mechanically compacting finely divided cathode materials into or onto the cathode current collector.

Some IMD batteries include compounds that may be corrosive to titanium or titanium-based alloys, such as by reacting with titanium atoms in the titanium or titanium-based alloy and forming compounds with undesirable properties. For example, some IMD batteries use fluorine-containing electrolytes to form an electrochemical cell, wherein the fluorine-containing electrolytes may react with titanium to form an electrically insulating film comprising titanium and fluorine at the surface of the titanium or titanium-based alloy. Over the life of the battery, this insulating fluorine-containing film may degrade the electrical contact between the cathode material and the cathode current collector. This, in turn, may increase the overall impedance of the battery, causing the battery to be produce less and less power over time.

It has been found that a titanium nitride (TiN) coating applied to a titanium current collector provides good corrosion resistance to fluorine-based electrolytes or other corrosive materials that may be used in IMDs. For example, applying a TiN coating to portions of a current collector surface has been found to provide for improved battery impedance stability over time. Moreover, TiN coatings exhibit high hardness and good electrical conductivity.

Several methods for forming a titanium nitride coating on titanium components have been used, including physical vapor deposition (PVD), such as magnetron sputtering PVD or cathodic arc physical vapor deposition (CAPVD). In some examples, for PVD deposition, a titanium-bearing species and a nitrogen-bearing species are supplied to the body to be coated. For example, in CAPVD, titanium may be vaporized and reacted with nitrogen to form TiN in a high-energy environment which then condenses on the surface of the titanium component. In addition to producing substantially atomic vapor, the CAPVD process may also result in the ejection of small globules of condensed titanium which may react with the nitrogen and may also be deposited on the surface of the titanium component.

The coating efficiency of PVD deposition onto more complex component geometries is typically poor because PVD generally only provides good thickness uniformity for surfaces that have a good line of sight to the deposition apparatus (e.g., surfaces that are orientated substantially normal to the primary direction of deposition flux). Because more complex geometries generally have many different surfaces having many different orientations, it is often difficult to effectively and uniformly coat all the surfaces without increasing the expense and complexity of the deposition process. For example, one method for accommodating complex component geometry and attempting to provide for substantially uniform deposition comprises translating or rotating the components through the deposition flux in order to expose the various surfaces of the component more completely to the deposition flux. While this method can improve coating uniformity, non-uniformities are typically not eliminated and this method adds considerable complexity to the deposition apparatus, reduces deposition apparatus throughput, and increases coating process cost.

Another concern with PVD deposition is that adhesion between the deposited material and the component may not be sufficiently strong, such that portions of the deposited coating may crack and/or flake off. Maintaining adequate coating adhesion requires careful tailoring of the deposition process and/or component cleaning process, which can substantially increase process complexity and cost.

In addition, a minimum film thickness is typically required to provide adequate corrosion protection in a given environment, however, the non-uniformities associated with PVD methods described above result in some areas of the coating being substantially thicker than necessary in order to assure that the thinnest areas of the coating have adequate thickness. Thicker films are more susceptible to cracking or flaking when the titanium component is manipulated.

Thermal nitriding provides an alternative method of forming a corrosion-resistant surface region of increased nitrogen concentration on one or more exposed surfaces of a titanium or titanium-based alloy component. As used herein, the term "surface region of increased nitrogen concentration" may refer to a region at or proximate an exposed surface that comprises at least one of titanium nitride (TiN), dititanium nitride ($Ti_2N$), or a solid solution of nitrogen dissolved into the material of the titanium or titanium-based alloy body (also referred to as a "nitrogen-enriched solution" or "nitrogen-enriched region"). Because many components in the IMD battery are made primarily or completely from titanium or a titanium-based alloy, thermal nitriding allows a surface region of increased nitrogen concentration to be formed at an exposed surface of the titanium or titanium-based alloy component by exposing the component to a nitrogen-bearing gas, such as nitrogen gas ($N_2$) or ammonia gas ($NH_3$) at an elevated temperature, such as between about 600° C. and about 880° C. as for the process described herein. The thermal nitriding results in a chemical reaction between nitrogen atoms within the nitrogen-bearing gas and titanium atoms at or near the surface of the titanium or titanium-based alloy component. Thermal nitriding may provide for exceptional coating uniformity, coating adhesion and repeatability afforded by the thermal process. Due to these advantages, the thermal nitriding processes of the present disclosure may allow for the selection of process conditions which provide excellent corrosion protection while minimizing overall coating thickness and thereby minimizing or avoid issues associated with relatively thicker coatings, such as coating spalling, cracking, or flaking.

For the case of titanium or titanium-based alloy components, the thermal nitriding process of the present disclosure overcomes many of the deficiencies of PVD deposition described above. For example, because the thermal nitriding process of the present disclosure involves the chemical reaction of nitrogen atoms within a nitrogen-bearing gas with titanium or other atoms within the component, the process may provide for substantially uniform and substantially complete coverage of even the most complex geometries that PVD methods may only be able to achieve with added complexity or expense, if at all. In addition, as noted above, non-uniformities associated with PVD processes may result in a coating that is substantially thicker than necessary in order to assure that the thinnest areas of the coating have adequate thickness. Thicker films are more susceptible to cracking or flaking when the titanium component is manipulated, e.g. if it is bent. As described below, in some examples, the thermal nitriding process of the present disclosure can produce adequate and substantially uniform coverage and corrosion resistance with a surface region as thin as about 100 nanometers or thinner. In some examples, this 100 nanometer corrosion-resistant surface region may be about 5% of the thickness of a CAPVD deposited coating (which often must be 2 micrometers or thicker in some places to provide adequate coverage). Thus, the corrosion-resistant surface region film formed by thermal nitriding may be less likely to crack or flake. Finally, because the thermal nitriding process of the present disclosure involves the formation of a surface region of increased nitrogen concentration within the component, such as by diffusing nitrogen atoms into the bulk and/or forming a TiN or $Ti_2N$ layer on the bulk of the titanium material, rather than depositing TiN onto the surface of the titanium, a corrosion-resistant surface region or film formed by thermal nitriding has a much stronger adhesion to the underlying titanium or titanium-based alloy component, and thus may be less likely to crack or flake off. In short, the thermal nitriding process described herein may provide corrosion resistance that is equally effective or superior to a PVD process, while providing several advantages over the PVD process, including reduced cost.

Many titanium components of IMDs are made from a commercially pure grade of titanium. For example, cathode current collectors may be made from Grade 1 titanium because Grade 1 titanium provides for good ductility during component formation, it can be easily welded, and exhibits good corrosion resistance in many chemical environments. However, when Grade 1 titanium is exposed to higher temperatures, e.g. above about 880° C., it transforms from primarily a hexagonal close packed structure (generally referred to as alpha-phase titanium) to primarily a body-centered cubic structure (generally referred to as beta-phase titanium). Upon cooling back to ambient temperature, the beta-phase titanium transforms back into alpha-phase titanium. The transition from the primarily alpha-phase titanium structure to the primarily beta-phase structure upon heating and then back to alpha-phase titanium upon cooling may cause a titanium component made from Grade 1 titanium to expand non-uniformly so that the component tends to become misshapen or warped. Because IMDs generally must be very small and its components must fit within a very small, confined space, unpredictable warping or other deformation of a component is undesirable. For this reason, a thermal nitriding process, which generally requires temperatures as high as 900° C. or more in order to provide thicker TiN films, was viewed unfavorably when it was to be used to provide a TiN coating on a Grade 1 titanium component to be used in an IMD.

It has been found, however, that a particularly thin, e.g., as thin as about 100 nanometers, for example between about 100 nanometers and about 200 nanometers, surface region of increased nitrogen concentration formed by thermal nitriding at relatively lower temperatures, e.g., between about 600° C. and about 880° C., for example between about 650° C. and about 870° C., such as between about 650° C. and about 750° C., is sufficient, depending on the chemical environment, to provide adequate coverage and corrosion resistance for titanium and titanium-based alloy components used in batteries of implantable medical devices. The thermal nitriding process described in the present disclosure can provide for a thin surface region of increased nitrogen concentration, such as a film or region comprising TiN, $Ti_2N$, or a nitrogen-enriched solid solution of nitrogen dissolved into the titanium or titanium-based alloy bulk of the component, that is formed at a temperature that is low enough that a component made from a commercially pure titanium, such as Grade 1 titanium, will be adequately covered with a surface region of increased nitrogen concentration without undesirable warping or other distortion of the component shape.

FIG. 1 is a conceptual diagram illustrating an example therapy system 10 that may be used to provide therapy to a patient 12. Patient 12 ordinarily, but not necessarily, will be a human. Therapy system 10 may include an implantable medical device (IMD) 16, such as an implantable cardiac device, and a programmer 24. In the example depicted in FIG. 1, IMD 16 is connected (or "coupled") to leads 18, 20, and 22 via a connector block 26. IMD 16 may be, for example, a device that provides cardiac rhythm management therapy, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

Leads 18, 20, 22 that are coupled to IMD 16 may extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver stimulation therapy to heart 14 by delivering stimulation to an extravascular tissue site in addition to or instead of delivering stimulation via electrodes of intravascular leads 18, 20, 22.

IMD 16 may sense electrical signals attendant to the depolarization and repolarization of heart 14 (e.g., cardiac signals) via electrodes coupled to at least one of the leads 18, 20, 22. In the example shown in FIG. 1, RV lead 18 carries electrodes 38A, 38B, and 38C, LV lead 20 carries electrodes 40A, 40B, and 40C, and RA lead 22 carries electrodes 42A, 42B, and 42C In some examples, IMD 16 provides pacing pulses to heart 14 based on the cardiac signals sensed within heart 14. The configurations of electrodes 38A, 38B, 38C, 40A, 40B, 40C, 42A, 42B, 42C used by IMD 16 for sensing and pacing may be unipolar or bipolar. IMD 16 may also provide defibrillation therapy and/or cardioversion therapy via electrodes 38A, 38B, 38C, 40A, 40B, 40C, 42A, 42B, 42C located on at least one of the leads 18, 20, 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies, e.g., shocks with increasing energy levels, until a fibrillation of heart 14 is stopped. IMD 16 may detect fibrillation by employing one or more fibrillation detection techniques known in the art. For example, IMD 16 may identify cardiac parameters of the cardiac signal, e.g., R-waves, and detect fibrillation based on the identified cardiac parameters.

In some examples, programmer 24 may be a handheld computing device or a computer workstation. Programmer 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, or patient 12 may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

Programmer 24 may communicate with IMD 16 via a wireless communication link 44 using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
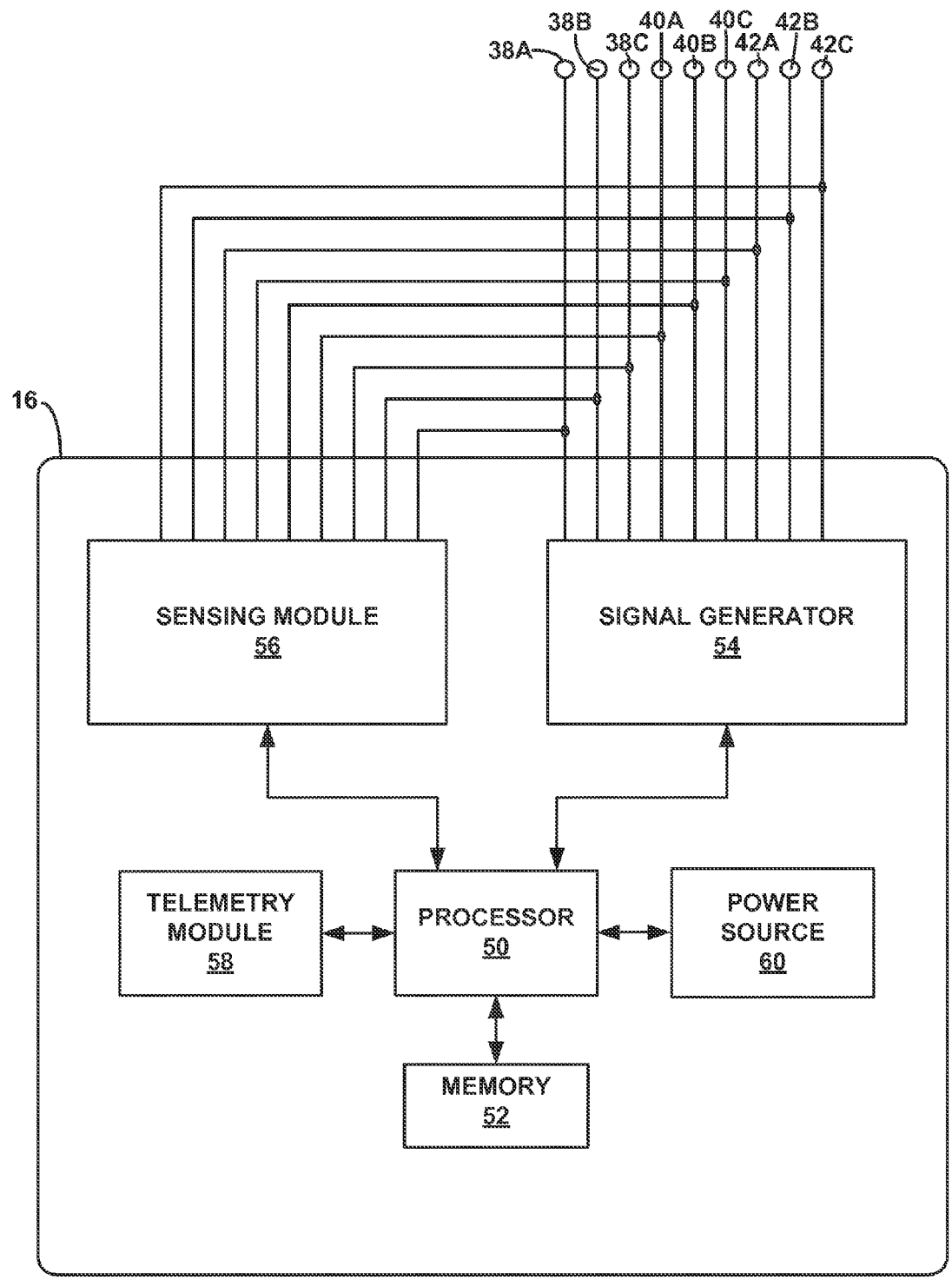
FIG. 2 is a functional block diagram illustrating an example configuration of an implantable medical device.

FIG. 2 is a functional block diagram illustrating an example configuration of IMD 16 that may be used to implement certain techniques of this disclosure. In the illustrated example, IMD 16 includes a processor 50, a memory 52, a signal generator 54, a sensing module 56, a telemetry module 58, and a power source 60.

Processor 50 may include any one or more of a microprocessor, a controller, a digital signal processor (DSP), an application specific integrated circuit (ASIC), a field-programmable gate array (FPGA), or equivalent discrete or analog logic circuitry. In some examples, processor 50 may include multiple components, such as any combination of one or more microprocessors, one or more controllers, one or more DSPs, one or more ASICs, and/or one or more FPGAs, as well as other discrete or integrated logic circuitry. The functions attributed to processor 50 in this disclosure may be embodied as software, firmware, hardware or any combination thereof.

In some examples, processor 50 controls signal generator 54 to deliver stimulation therapy to heart 14 according to a selected one or more of therapy programs, which may be stored in memory 52. For example, processor 50 may control signal generator 54 to deliver electrical pulses with the amplitudes, pulse widths, frequency, or electrode polarities specified by the selected one or more therapy programs.

Memory 52 may be a non-transitory, computer-readable storage medium that includes computer-readable instructions that, when executed by processor 50, cause IMD 16 and processor 50 to perform various functions attributed to IMD 16 and processor 50 in this disclosure. Memory 52 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Signal generator 54 is electrically coupled to electrodes 38A, 38B, 38C, 40A, 40B, 40C, 42A, 42B, 42C, e.g., via conductors of the respective leads 18, 20, 22. In some examples, signal generator 54 is configured to generate and deliver electrical stimulation therapy to heart 14. For example, signal generator 54 may deliver defibrillation shocks as therapy to heart 14 via at least two of tip electrodes 38A, 40A, 42A. Signal generator 54 may deliver pacing pulses via ring electrodes 38B, 40B, 42B coupled to leads 18, 20, and 22, respectively, and/or helical electrodes 38C, 40C, and 42C of leads 18, 20, and 22, respectively. In some examples, signal generator 54 delivers pacing, cardioversion, or defibrillation stimulation in the form of electrical pulses. In other examples, signal generator 54 may deliver one or more of these types of stimulation in the form of other signals, such as sine waves, square waves, or other substantially continuous time signals.

Signal generator 54 may include a switch module, and processor 50 may use the switch module to select which of the available electrodes are used to deliver such stimulation. The switch module may include a switch array, switch matrix, multiplexer, or any other type of switching device suitable to selectively couple stimulation energy to selected electrodes.

Sensing module 56 may be included in IMD 16 to monitor signals from at least one of electrodes electrodes 38A, 38B, 38C, 40A, 40B, 40C, 42A, 42B, 42C in order to monitor electrical activity of heart 14. Sensing module 56 may also include a switch module. In some examples, processor 50 may select the electrodes that function as sense electrodes via the switch module within sensing module 56. Sensing module 56 may include one or more detection channels (not shown), each of which may comprise an amplifier. The detection channels may be used to sense the cardiac signals. Some detection channels may detect cardiac events, such as R- or P-waves, and provide indications of the occurrences of such events to processor 50. One or more other detection channels may provide the signals to an analog-to-digital converter, for processing or analysis by processor 50. In some examples, processor 50 may store the digitized versions of signals from one or more selected detection channels in memory 52 as EGM signals. In response to the signals from processor 50, the switch module within sensing module 56 may couple selected electrodes to selected detection channels, e.g., for detecting events or acquiring an EGM in a particular chamber of heart 14.

Telemetry module 58 in IMD 16, as well as telemetry modules in programmers, such as programmer 24, may accomplish communication by RF communication techniques. In addition, telemetry module 58 may communicate with programmer 24 via proximal inductive interaction of IMD 16 with programmer 24. Processor 50 controls telemetry module 58 to send and receive information.

Power source 60 delivers operating power to various components of IMD 16. Power source 60 may include a small rechargeable or non-rechargeable battery and a power generation circuit to produce the operating power. In some examples, the battery of power source 60 may charge one or more capacitors to provide a pulse, for example to provide a cardioversion or defibrillation pulse, or to provide a pulse of electrical energy sufficient to drive a pumping mechanism, such as an electromechanical piston pump for infusing a therapeutic agent into patient 12.

Figure 3:
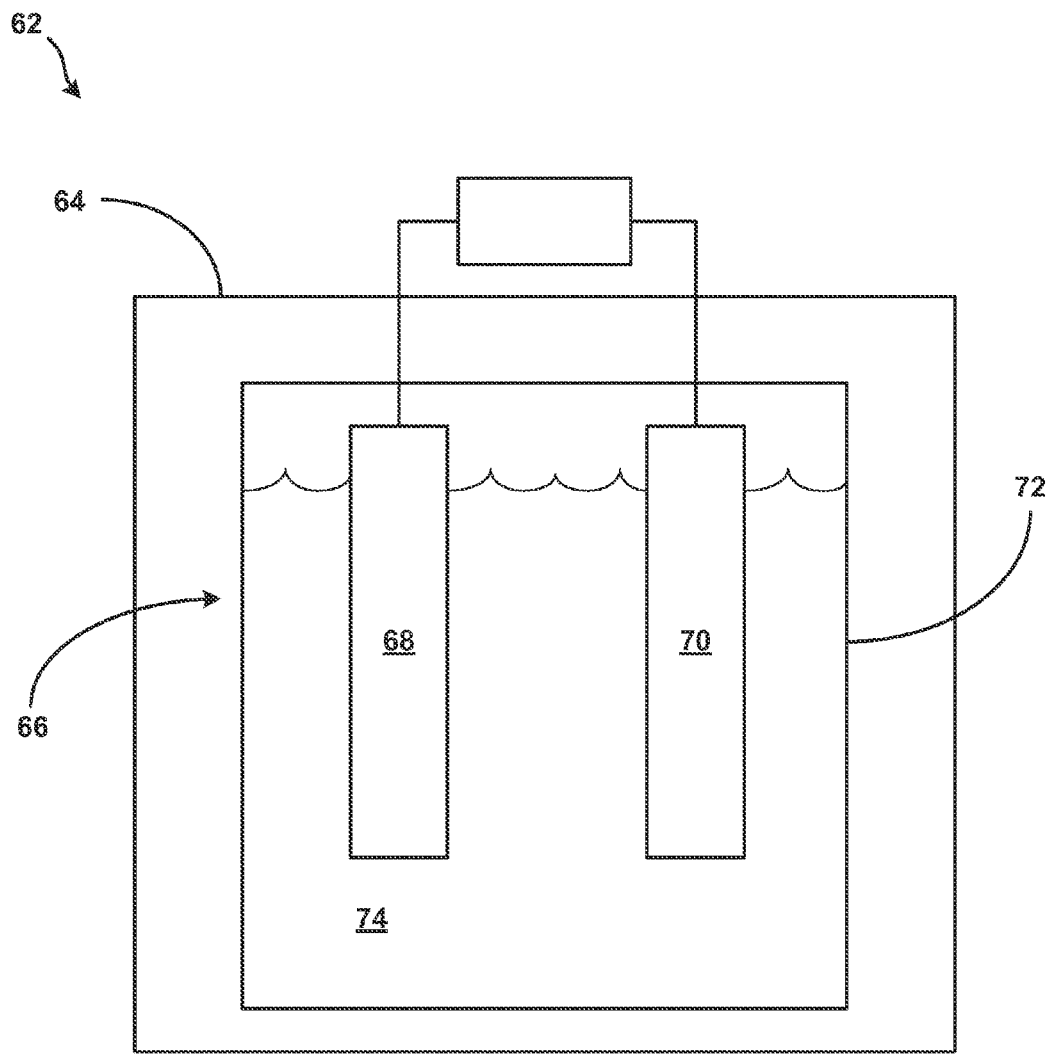
FIG. 3 is a schematic diagram illustrating an example configuration of a battery that may be used as the power source for the implantable medical device of FIG. 2.

FIG. 3 is a conceptual schematic diagram showing a battery 62 that may be used as part of a power source for an implantable medical device, such as power source 60 of IMD 16 shown in FIG. 2. As shown in FIG. 3, battery 62 comprises a battery housing 64 enclosing an electrochemical battery cell 66. Battery cell 66 comprises an anode 68, a cathode 70, and a compartment 72 containing an electrolyte 74, wherein anode 68 and cathode 70 are in contact with electrolyte 74 in order to generate electrical energy from chemical reactions between anode 68, cathode 70, and electrolyte 74. In some examples (not shown), the battery cell may comprise two compartments, each containing a different electrolyte. In such an arrangement, one of the anode or the cathode is in contact with the first electrolyte, while the other of the anode or the cathode is in contact with the second electrolyte. Battery 62 may also comprise wiring or conductors 76 to electrically connect anode 68 and cathode 70 to terminals that may be connected to electronics 78, such as the circuitry of IMD 16 described above (e.g., processor 50, memory 52, signal generator 54, sensing module 56, and telemetry module 58). In one example, described in more detail below, cathode 70 comprises a cathode current collector that provides for mechanical support of a cathode material used to form cathode 70 and for electrical contact between the cathode material and the current collector, for example when the cathode material comprises a mixture of material in a finely divided form, such as powders or particulates.

As noted above, it is generally desirable to minimize the total volume of a particular IMD, and consequently, it is generally desirable to minimize the volume of components within the IMD, such as components of the IMD battery. However, an IMD battery must satisfy requirements of the specific applications that the IMD will be used for, including total energy and peak power. For a particular battery, the total energy available is generally proportional to the volume of anode and cathode materials, while the peak power output is generally proportional to the surface area of the anode and cathode electrodes. For IMD applications requiring low to moderate powers, such as monitoring devices and pacemakers, sufficient cathode surface area may be obtained by simply pressing the required cathode powder volume into a current collector in the shape of a cup or ring which can then be inserted into the battery encasement in the "as-pressed" condition. For the case of IMD applications with high power requirements, such as implantable cardioverter defibrillators (ICDs), the required cathode surface area is sufficiently large that additional design complexities and fabrication steps may be required. The larger surface area of high-power cathode current coupled with the general desire to reduce IMD component volume typically results in a current collector having a complex geometry. However, as noted above, coating a complex geometry with PVD processes is challenging because of line-of-sight issues for the deposition apparatus.

FIG. 4 shows an example cathode current collector 80 that may be used for a high-power battery, e.g., a battery that powers an IMD requiring relatively high discharge rates, such as the implantable cardiovertor-defibrillator (ICD) device 16 described above with respect to FIG. 1. In one example, current collector 80 comprises a complex geometry in order to enable fabrication of a relatively thin cathode having a relatively large surface area, and thus increase the rate at which energy can be discharged from battery 62. In this disclosure, the term "complex geometry" refers to a geometry where one or more structures within the geometry includes a surface or surfaces that would not have a direct line of sight if a PVD or CVD process were used to attempt depositing a coating, such as a TiN corrosion-resistant coating. In the example shown in FIG. 4, current collector 80 comprises a mesh screen or perforated sheet 82, for example comprising a plurality of wires or fibers 94, that provides a relatively large surface area for electrically contacting and mechanically support a cathode material while still providing a relatively small physical volume.

The relatively large surface area of perforated sheet 82 provides for a relatively large surface area of cathode material and therefore a relatively high rate of discharge, for example for cardioversion or defibrillation shocks. However, because in some examples current collector 80 is used in an implantable medical device, such as IMD 16 shown in FIG. 1, is may be undesirable for the current collector 80, in its final form, to occupy the relatively large footprint of current collector 80 shown in FIG. 4. Therefore, in some examples, current collector 80 is configured to be into as small of a volume as is practical in order to provide the smallest possible battery 62, and in turn the smallest possible implantable medical device.

As described above, titanium is often used to manufacture components of implantable medical devices. In one example, cathode current collector 80 is made from titanium. In some examples, current collector 80 is made from a commercially pure grade of titanium, such as Grade 1 titanium (less than about 0.08 at. % carbon (C), less than about 0.18 at. % oxygen (O), less than about 0.03 at. % nitrogen (Ni), less than about 0.2 at. % iron (Fe), and less than about 0.015 at. % hydrogen (H), with the balance being titanium (Ti)). Other grades of titanium that may be used include, but are not limited to, Grade 2 titanium, Grade 3 titanium, and Grade 4 titanium. An example of a titanium-based alloy that may be used is Grade 7 titanium, although other titanium-based alloys may be used. In one example, current collector 80 consists essentially of a commercially-pure grade of titanium. In one example, current collector 80 consists of a commercially-pure grade of titanium, such as Grade 1 titanium.

Figure 6:
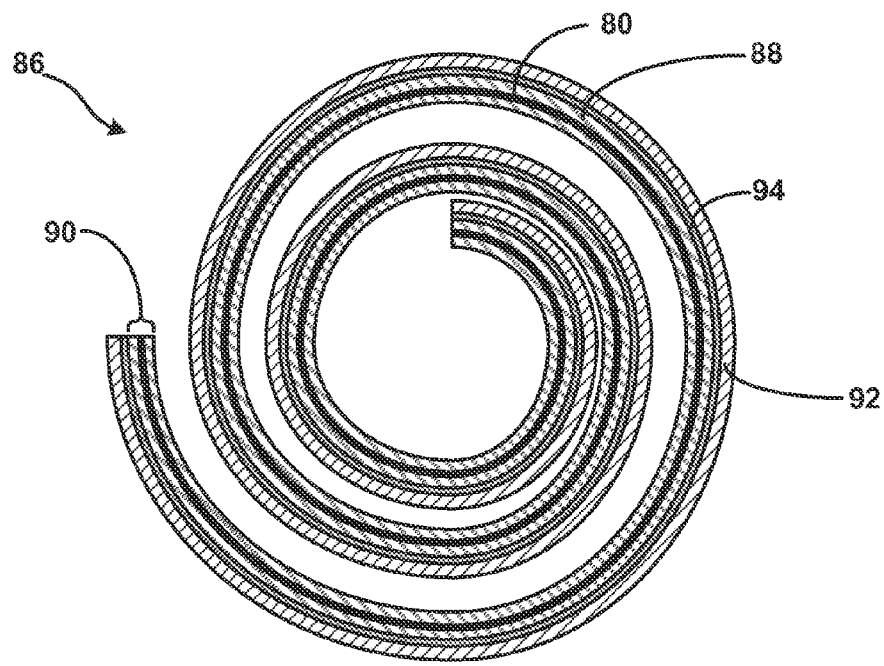
FIG. 6 is a cross-sectional view showing the battery electrode assembly of FIG. 5 rolled into a spiral in order to fit into a smaller space within the implantable medical device battery.

In one example, current collector 80 is combined with other components of battery 62 to form an electrode assembly that is used in battery 62. FIG. 5 shows a cross-sectional view of an example battery electrode assembly 86 constructed from a cathode current collector, such as current collector 80 shown in FIG. 4, which is embedded or pressed into a powder of a cathode material 88 to form a cathode composite subassembly 90. Cathode composite subassembly 90 is mated with an anode material 92 with an electrically insulating separator 94 sandwiched between cathode composite subassembly 90 and anode 92. Cathode material 88 used to form cathode composite subassembly 90 may comprise at least one of manganese dioxide, fluorinated carbon, silver vanadium oxide, or mixtures thereof. Anode 92 may be made from a material that comprises a metallic lithium sheet. Separator 94 may be formed from a porous, electrically insulating material, such as a porous polymeric material, for example at least one of polyethylene, polypropylene, and polytetrafluoroethylene. In one example, battery electrode assembly 86 is placed within a battery compartment containing an electrolyte, such as battery compartment 72 containing electrolyte solution 74 described above with respect to FIG. 3, so that both cathode composite subassembly 90 and anode 92 are contacted by the electrolyte solution. Further example electrode assemblies that may be used in a battery of an IMD are described in the commonly assigned U.S. Pat. No. 5,180,642, issued Jan. 19, 1993, entitled "Electrochemical Cells With End-Of-Service Indicator," and U.S. Pat. No. 7,824,805, issued Nov. 2, 2010, entitled "Implantable Medical Device Battery," the entire contents of which are incorporated by reference as if reproduced herein To further reduce the overall size of battery 62, in some examples, battery electrode assembly 86 may be folded, bent, rolled, or compacted. FIG. 6 shows a cross-sectional view of the example battery electrode assembly 86 of FIG. 5 after it has been compacted in order to reduce the overall size of battery electrode assembly 86 so that the implantable medical device may be as small as possible. As shown in the example of FIG. 6, battery electrode assembly 86 has been rolled into a spiral-shaped structure wherein battery electrode assembly 86 is rolled up upon itself. In some examples, the rolled, bent, or otherwise compacted battery electrode assembly 86 is placed into battery cell 66 so that anode 92 and cathode subassembly 90 are in contact with the electrolyte within battery cell 66. Cathode subassembly 90 and anode 92 are then electrically coupled to the electronics 78 of the implantable medical device that battery 62 is powering, such as processor 50, memory 52, signal generator 54, sensing module 56, and telemetry module 58 described above with respect to FIG. 2. Although the example of FIG. 6 shows some opening between different passes of the spiral, in some examples, the spiral may be wound much tighter so as to reduce the overall size of battery electrode assembly 86 to as small as possible.

The rolling, bending, or otherwise compacting components of battery electrode assembly 86 may put stress on corrosion-resistant coatings formed on one or more of the components of electrode assembly 88. This stress may cause the coating to crack, flake, or spall, exposing the underlying bulk material of the component to the potentially corrosive materials within battery 62. As described above, for titanium components, it has been found that titanium nitride (TiN) provides good corrosion resistance, such as against corrosive effects of fluorine-containing electrolytes that may be used in battery 62. Titanium nitride coatings, however, are brittle and may crack or flake off titanium components due to stresses induced by bending or rolling of the underlying component. For the case of PVD TiN film depositions, in some instances, it may be possible to mitigate the deleterious effects of stress on the coating by masking the components such that the regions of highest stress remain uncoated. Care may also be taken to assure good PVD film adhesion to the underlying component and to minimize the coating thickness while still providing adequate corrosion protection. Therefore, while PVD TiN films can exhibit good performance in IMD battery applications, the steps necessary to assure good PVD TiN film performance result in a complicated, high cost coating process. The corrosion-resistant surface region of increased nitrogen concentration that may be formed by a thermal nitriding processing according to the present disclosure, such as a region or film comprising at least one of TiN, $Ti_2N$, and a solid solution of nitrogen dissolved into the titanium or titanium-based alloy bulk, may produce a corrosion-resistant surface region or film on the titanium or titanium-based alloy that exhibits substantially complete and relative strong bonding to the titanium or titanium-based alloy. Furthermore, the thermal nitriding process may yield substantially uniform film thickness even for complex component geometries.

Figure 7:
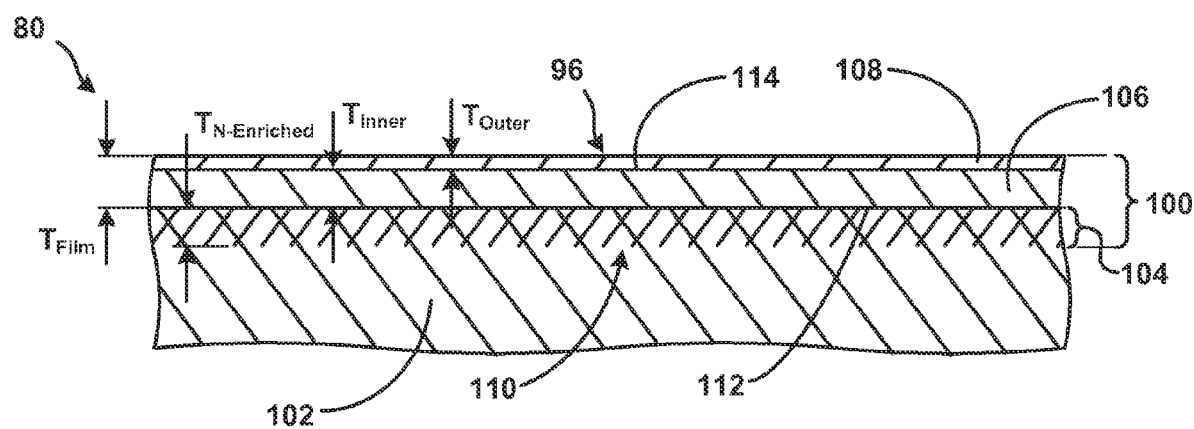
FIG. 7 is a cross-sectional conceptual diagram illustrating a surface of the example current collector of FIG. 4, wherein a corrosion-resistant surface region of increased nitrogen concentration has been formed at the surface.

FIG. 7 show conceptual close-up views of an exposed surface of a titanium or titanium-based alloy component with examples of a corrosion-resistant surface region of increased nitrogen concentration that may be formed on the titanium or titanium-based alloy bulk of the component. FIG. 7 is described herein as referring to a corrosion-resistant surface region 100 on a current collector 80, such as cathode current collector 80 described above with respect to FIGS. 4-6. The corrosion-resistant surface region 100 may be formed on other titanium or titanium-based alloy components, however, in order to protect exposed surfaces of the component from a corrosive environment, such as the fluorine-containing electrolytes in battery 62. Other examples of titanium or titanium-based alloy components that may be protected by a corrosion-resistant surface region 100 in accordance with the present disclosure include, but are not limited to, a feedthrough assembly for sealing the battery from other components of the IMD while allowing an electrically-conductive pin to pass through or components thereof, such as a ferrule or the pin, or the battery housing, such as battery compartment 72 described above with respect to FIG. 3.

In one example, the component upon which corrosion-resistant region 100 is formed comprises titanium, titanium-based alloys, and composites thereof. Composites, as used herein, refer to materials that comprise a physical mixture of titanium and titanium-based alloys. In one example, the component consists essentially of titanium, titanium-based alloys, and composites thereof. The term "consisting essentially of titanium, titanium containing alloys, and composites thereof," as it is used herein, refers to a material with a negligible amount of other impurities so that corrosion-resistant surface region 100 may be formed to substantially cover an exterior surface of the component, such as current-collecting surface 96 described below. In some examples, "consisting essentially of" refers to the component comprising negligible impurities so that corrosion-resistant surface region 100 substantially continuously covers the exterior surface with no pockets or exposed portions due to impurities. In one example, the component consists of titanium, titanium-based alloys, and composites thereof. In one example, the component consists essentially of a commercially pure grade of titanium, such as grade 1 titanium. In one example, the component consists of a commercially pure grade of titanium, such as grade 1 titanium.

FIG. 7 shows an example current collector 80, where a corrosion-resistant surface region 100 has been formed on titanium or titanium-based alloy bulk 102 at current-collecting surface 96. In the example of FIG. 7, corrosion-resistant surface region of increased nitrogen concentration 100 comprises a region 104 where nitrogen has diffused and dissolved into titanium or titanium-based alloy bulk 102, also referred to herein as nitrogen-enriched region 104 and a film comprising a bilayer formed on region 104, with the bilayer comprising an inner layer 106 proximate nitrogen-enriched region 104 and an outer layer 108 proximate surface 96.

Figure 8:
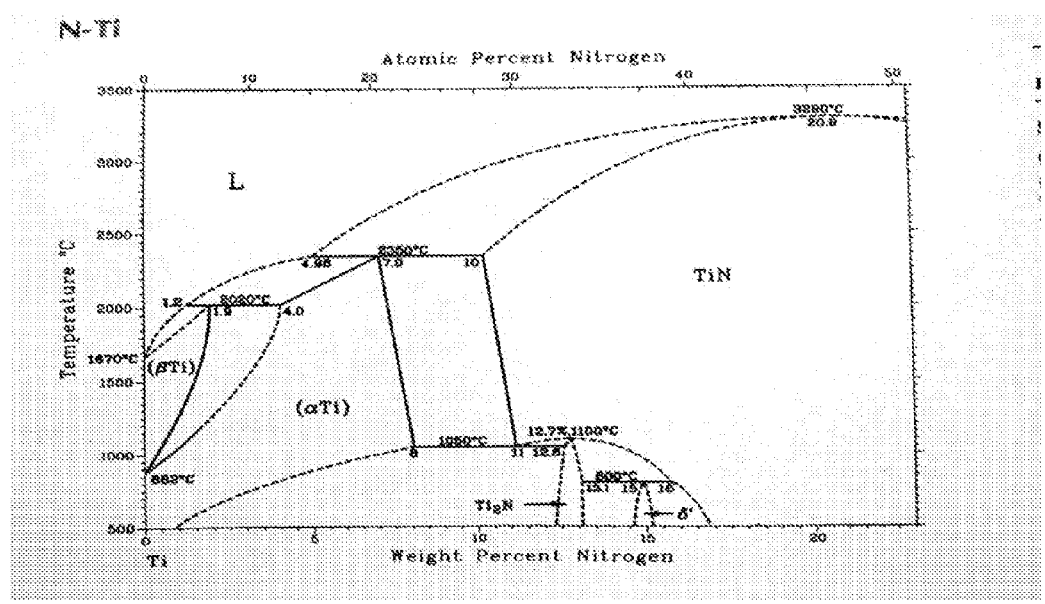
FIG. 8 is a partial phase diagram for titanium and nitrogen.

In one example, nitrogen-enriched region 104 comprises a solid solution of nitrogen dissolved into the titanium or titanium-based alloy that forms bulk 102 and exhibits increased nitrogen content relative to the nitrogen content of bulk 102. Nitrogen-enriched region 104 may be formed by nitrogen atoms diffusing into the titanium or titanium-based alloy of current collector 80 and dissolving. Nitrogen-enriched region 104 is shown conceptually in FIG. 7 as generally overlapping with the titanium or titanium-based alloy bulk 102. As shown conceptually in FIG. 7, there is not a defined boundary between nitrogen-enriched region 104 and the titanium or titanium-based alloy bulk 102. Rather, experimental depth profiles of example surface regions of increased nitrogen concentration 100 show a gradual, generally exponential decrease in the elemental concentration of nitrogen within nitrogen-enriched region 104 such that there is a diffuse boundary 110 with the underlying titanium or titanium-based alloy of bulk 102. Given the range of nitrogen concentrations, based on prior reported phase diagrams of titanium and nitrogen (see, e.g., FIG. 8), it is possible that a composite of several phases of titanium and nitrogen may be present within corrosion resistant surface region 100.

In one example, inner layer 106 formed on nitrogen-enriched region 104 comprises dititanium nitride ($Ti_2N$) and outer layer 108 comprises titanium nitride (TiN). The film formed by inner layer 106 and outer layer 108 has an overall thickness $T_{Film}$ from surface 96 to nitrogen-enriched region 104 that is relatively small compared to the overall thickness of current collector 80. The thickness $T_{Film}$ of corrosion resistant region 100 includes the thickness $T_{Inner}$ of inner layer 106 (e.g., the $Ti_2N$ layer) and the thickness $T_{Outer}$ of outer layer 108 (e.g., the TiN layer).

In one example, the thickness $T_{Outer}$ of outer layer 108 (e.g., the TiN layer) may be substantially equal to zero such that surface region of increased nitrogen concentration 100 comprises substantially only a nitrogen-enriched region 104 and an inner layer 106 (e.g., the $Ti_2N$ layer). It is believed that in some chemical environments that only a nitrogen-enriched region 104 and a layer 106 (e.g., a $Ti_2N$ layer) may be sufficient to prevent or reduce corrosion of the titanium or titanium-based alloy bulk 102. In another example, both the thickness $T_{Inner}$ of inner layer 106 (e.g., the $Ti_2N$ layer) and the thickness $T_{Outer}$ of outer layer 108 (e.g., the TiN layer) are substantially equal to zero such that surface region of increased nitrogen concentration 100 comprises substantially only a nitrogen-enriched region 104. It is believed that in some chemical environments that only a nitrogen-enriched region 104, e.g., a solid solution of nitrogen dissolved in the titanium or titanium-based alloy bulk 102, may be sufficient to prevent or reduce corrosion of the titanium or titanium-based alloy bulk 102.

The thicknesses of each layer or region, e.g., thickness $T_{Inner}$ of inner layer 106, thickness $T_{Outer}$ of outer layer 108, and thickness $T_{N-Enriched}$ of nitrogen-enriched region 104, and the overall thickness of surface region of increased nitrogen concentration 100, may depend on several factors of the thermal nitriding process, including, but not limited to nitrogen-bearing gas partial pressure applied, nitrogen-bearing gas composition (e.g. the concentrations of $N_2$ gas and $NH_3$ gas), total gas pressure applied, total gas composition, temperature applied, the amount of time that current collector 80 is subjected to elevated temperatures, and the temperature profile.

In one example, the thickness $T_{Film}$ (e.g., the combined thickness of inner layer 106 and outer layer 108) is less than about 0.5 micrometers (about 500 nanometers). In one example, thickness $T_{Film}$ is between about 0.1 micrometers (about 100 nanometers) and about 5 micrometers (about 5000 nanometers), such as between about 0.2 micrometers (about 200 nanometers) and about 1 micrometer (about 1000 nanometers). As noted above, it has been found that a corrosion-resistant film 100A grown by thermal nitriding having a thickness $T_{Film}$ of as little as about 100 nanometers (about 0.1 micrometers) may be sufficient in some chemical environments to provide adequate corrosion resistance for current collector 80. In other chemical environments, a thickness $T_{Film}$ of as little as about 200 nanometers (about 0.2 micrometers) may be sufficient to provide adequate corrosion resistance for current collector 80. In some examples, the total thickness $T_{N-Enriched}$ may be substantially thicker than the thickness $T_{Film}$ of layers 106 and 108. In one example, $T_{N-Enriched}$ may be as large as 20 micrometers or more.

As noted above, it has been found that nitrogen-enriched region 104, e.g., a solid solution of nitrogen dissolved into the titanium or titanium-based alloy bulk 102, may also provide some corrosion resistance to current collector 80.

Although the boundary 112 between inner layer 106 (e.g., the $Ti_2N$ layer, if present) and nitrogen-enriched region 104 and the boundary 114 between inner layer 106 (e.g., the $Ti_2N$ layer) and outer layer 108 (e.g., the TiN layer, if present) are shown as a sharp, well defined boundary, the location of the boundary relative to the free surface of the component may vary from location to location on the surface, as dictated by the underlying component microstructure.

Whether the corrosion-resistant surface region of increased nitrogen concentration comprises only a nitrogen-enriched region 104, a nitrogen-enriched region 104 and a layer 106 (e.g., a $Ti_2N$ layer), or a nitrogen-enriched region 104, an inner layer 106 (e.g., a $Ti_2N$ layer), and an outer layer (e.g., a TiN layer) will depend on parameters of the thermal nitriding process, described in more detail below. As described in more detail below, in general, shorter processing times and lower temperatures tend to favor the formation of thinner layers (e.g., smaller values for $T_{N-enriched}$, $T_{Inner}$, and $T_{Outer}$) as well as less TiN formation, e.g., a thinner or non-existent outer TiN layer 108.

Figure 9:
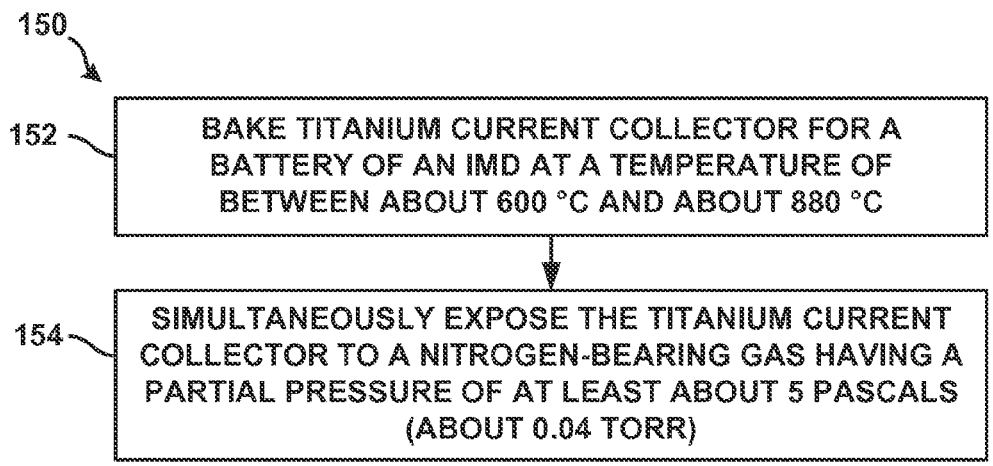
FIG. 9 is a flow diagram illustrating an example method of forming a corrosion-resistant surface region on a titanium or titanium-based alloy component using thermal nitriding.

FIG. 9 is a flow diagram of an example method 150 of making a titanium or titanium-based alloy component, such as a cathode current collector 80, having a corrosion-resistant surface region 100 made by a thermal nitriding process. The example method 150 of FIG. 9 comprises baking a component of an implantable medical device, such as the current collector 80 of IMD 16, at a temperature of between about 600° C. and about 880° C. (152), for example at a temperature of between about 650° C. and about 870° C., such as between about 650° C. and about 750° C. or between 800° C. and about 850° C., wherein the component comprises titanium, a titanium-based alloy, or composites thereof. The method 150 further comprises substantially simultaneous to baking the component, exposing the component to a nitrogen-bearing gas, such as $N_2$ gas, $NH_3$, or a mixture thereof, having a partial pressure (e.g., the partial pressure of the nitrogen-bearing components, e.g., partial pressure of $N_2$ gas and/or partial pressure of $NH_3$ gas) of at least about 5 pascals (about 0.04 torr), such as, e.g., at least about 2.5 kilopascals (about 18.7 torr), so that a corrosion-resistant surface region 100 of increased nitrogen concentration, such as a surface region 100 comprising at least one of titanium nitride (TiN), dititanium nitride ($Ti_2N$), or nitrogen dissolved in titania or a titanium-based alloy, forms at an exposed surface of the component (154). In one example, the resulting corrosion-resistant surface region 100 has a film thickness $T_{Film}$ of between about 0.1 micrometers and about 5 micrometers, such as between about 0.2 micrometers and about 1 micrometer. In another example, corrosion-resistant surface region 100 has a film thickness $T_{Film}$ of less than about 0.5 micrometers.

Figure 10:
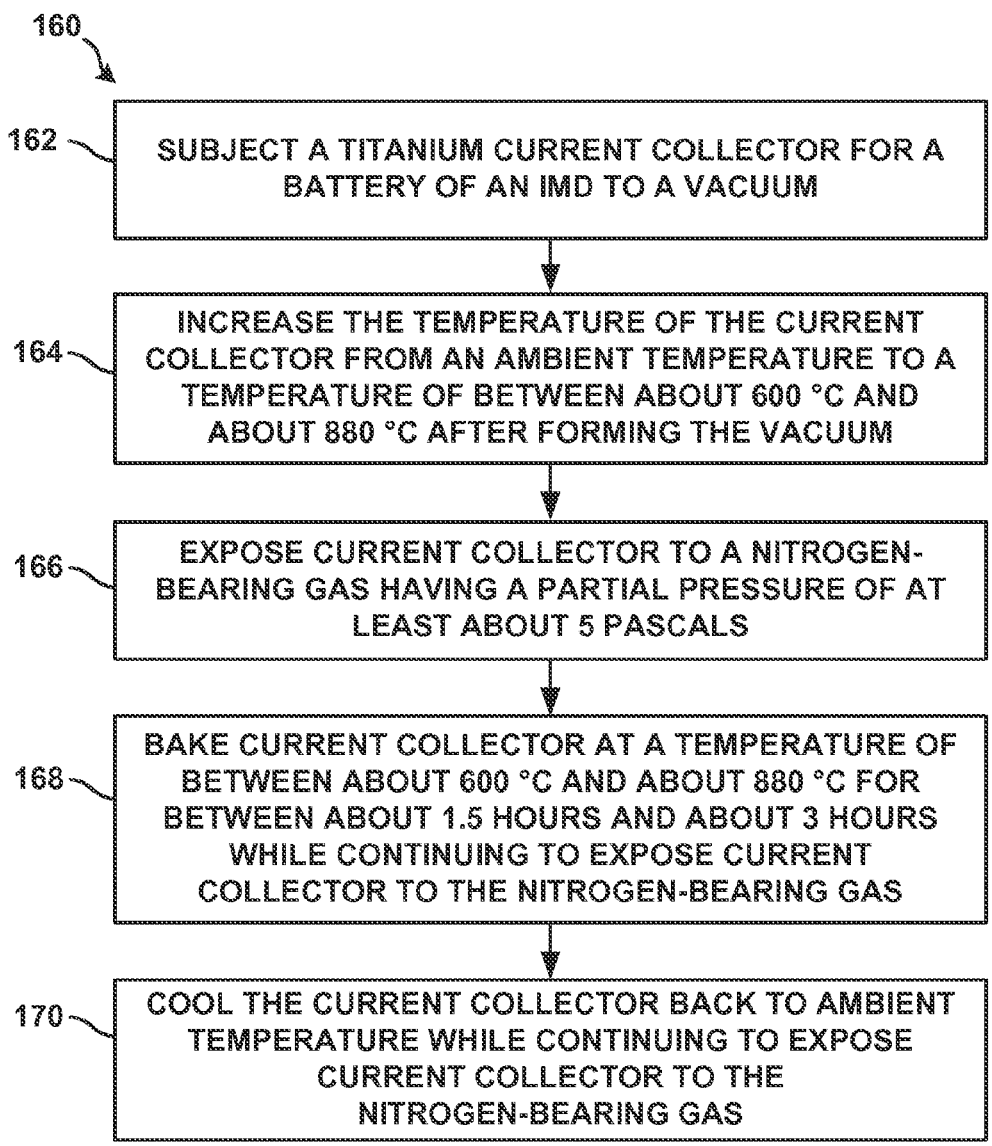
FIG. 10 is a flow diagram illustrating another example method of forming a corrosion-resistant surface region on a titanium or titanium-based alloy component using thermal nitriding.

FIG. 10 is a flow diagram of another example method 160 of making a titanium component, such as a cathode current collector 80. The example method 160 of FIG. 10 comprises subjecting a titanium or titanium-based alloy current collector 80 for a battery of an implantable medical device to a vacuum (162), such as battery 62 of IMD 16, increasing the temperature of current collector 80 from an ambient temperature, such as room temperature (e.g., about 20° C.), to between about 600° C. and about 880° C., for example to between about 650° C. and about 870° C., after forming the vacuum (164). The example method 160 further comprises exposing current collector 80 to a nitrogen-bearing gas having a partial pressure (e.g., the partial pressure of the nitrogen-bearing components, e.g., partial pressure of $N_2$ gas and/or partial pressure of $NH_3$ gas) of at least about 5 pascals (about 0.04 torr) (166), such as, e.g., at least about 2.5 kilopascals (about 18.7 torr). Current collector 80 is baked at a temperature of between about 600° C. and about 880° C. for between about 1.5 hours and about 3 hours while continuing to expose current collector 80 to the nitrogen-bearing gas (168), followed by cooling current collector 80 back down to the ambient temperature (e.g., room temperature at about 20° C.) while continuing to expose current collector 80 to the nitrogen-bearing gas (170).

In one example, the treating of titanium current collector 80 is performed within a vacuum furnace. In such examples, current collector 80 is placed in the furnace, the furnace is evacuated until the desired vacuum pressure is reached (162), the furnace gradually heats current collector 80 to the desired baking temperature (164), the nitrogen-bearing gas is introduces by supplying a flow of nitrogen-bearing gas to the furnace until the desired nitrogen-bearing gas partial pressure within the furnace is achieved (166), the furnace is held at the baking temperature (also referred to as a "soak temperature") for the desired period of time (168), and the furnace is allowed to cool while still feeding nitrogen-bearing gas to the furnace (170). In one example, subjecting current collector 80 to a vacuum (162) comprises, after placing current collector 80 in the furnace, evacuating the furnace to an absolute pressure of between about 0.005 pascal (about $3.7 \times 10^{-5}$ torr) and about 0.025 pascal (about $1.9 \times 10^{-4}$ torr). In one example, increasing the temperature of current collector (164) comprises increasing the temperature of the furnace at a rate of between about 10° C. per minute and about 50° C. per minute, for example about 20° C. per minute, to a final temperature of between about 600° C. and about 880° C., such as between about 650° C. and about 870° C., for example between about 800° C. and about 850° C.

In one example, exposing current collector 80 to the nitrogen-bearing gas (166) comprises supplying nitrogen gas ($N_2$) to the furnace until the nitrogen partial pressure is about 4 kilopascals (about 30 torr). In one example, exposing current collector 80 to the nitrogen-bearing gas (166) comprises supplying nitrogen gas ($N_2$) to the furnace until the nitrogen partial pressure is about 5 pascals (about 0.04 torr). In one example, exposing current collector 80 to nitrogen-bearing gas (166) comprises feeding a constant flow of nitrogen gas ($N_2$) to the furnace after the furnace has reached a predetermined temperature, and continuing to feed the nitrogen gas to the furnace while baking and cooling current collector 80. In some examples, the flow rate of nitrogen gas into the furnace may be between about 0.15 standard cubic meters per minute (about 5.3 standard cubic feet per minute) of nitrogen gas and about 0.3 standard cubic meters per minute (about 10.6 standard cubic feet per minute) of nitrogen gas, such as about 0.23 standard cubic meters per minute (about 8 standard cubic feet per minute). In some examples, the flow rate of nitrogen gas into the furnace may be 0.001 standard cubic meters per minute. Although some example process pressures and gas flow rates are specifically describe in this disclosure, other suitable pressure and flow rates values outside the example ranges are contemplated and are within the scope of the present disclosure. In some examples, the predetermined temperature upon which the feed of nitrogen gas is started may be between about 300° C. and about 600° C., such as between about 400° C. and about 500° C., for example at about 450° C.

In one example, baking current collector 80 (168) comprises holding the temperature of furnace at about 650° C., e.g. for between about 1 hour and about 3 hours. In another example, baking current collector 80 (168) comprises holding the temperature of the furnace at about 750° C., e.g., for between about 1 hour and about 3 hours. In yet another example, baking current collector 80 (168) comprises holding the temperature of the furnace at about 850° C., e.g., for between about 1 hour and about 3 hours. In one example, cooling current collector 80 (170) comprises allowing furnace to cool while continuing to feed the nitrogen-bearing gas to the furnace in order to expose current collector 80 to nitrogen.

EXAMPLES

Experimental Procedures

Multiple samples of current collectors similar to current collector 80 shown in FIG. 4 were fabricated from grade 1 titanium. Several sample current collectors were thermally nitrided to produce a corrosion-resistant surface region of increased nitrogen concentration at an exposed surface (Examples 1-4) using the procedures described below. A TiN film was deposited on one sample current collector via cathodic arc physical vapor deposition (CAPVD) (Comparative Example 5) as described below. Two sample current collectors were given no surface coating or treatment (Comparative Example 6). The resulting samples described in Examples 1-4 and in Comparative Examples 5 and 6 were tested using the following techniques.

X-Ray Diffraction Analysis

Figure 11:
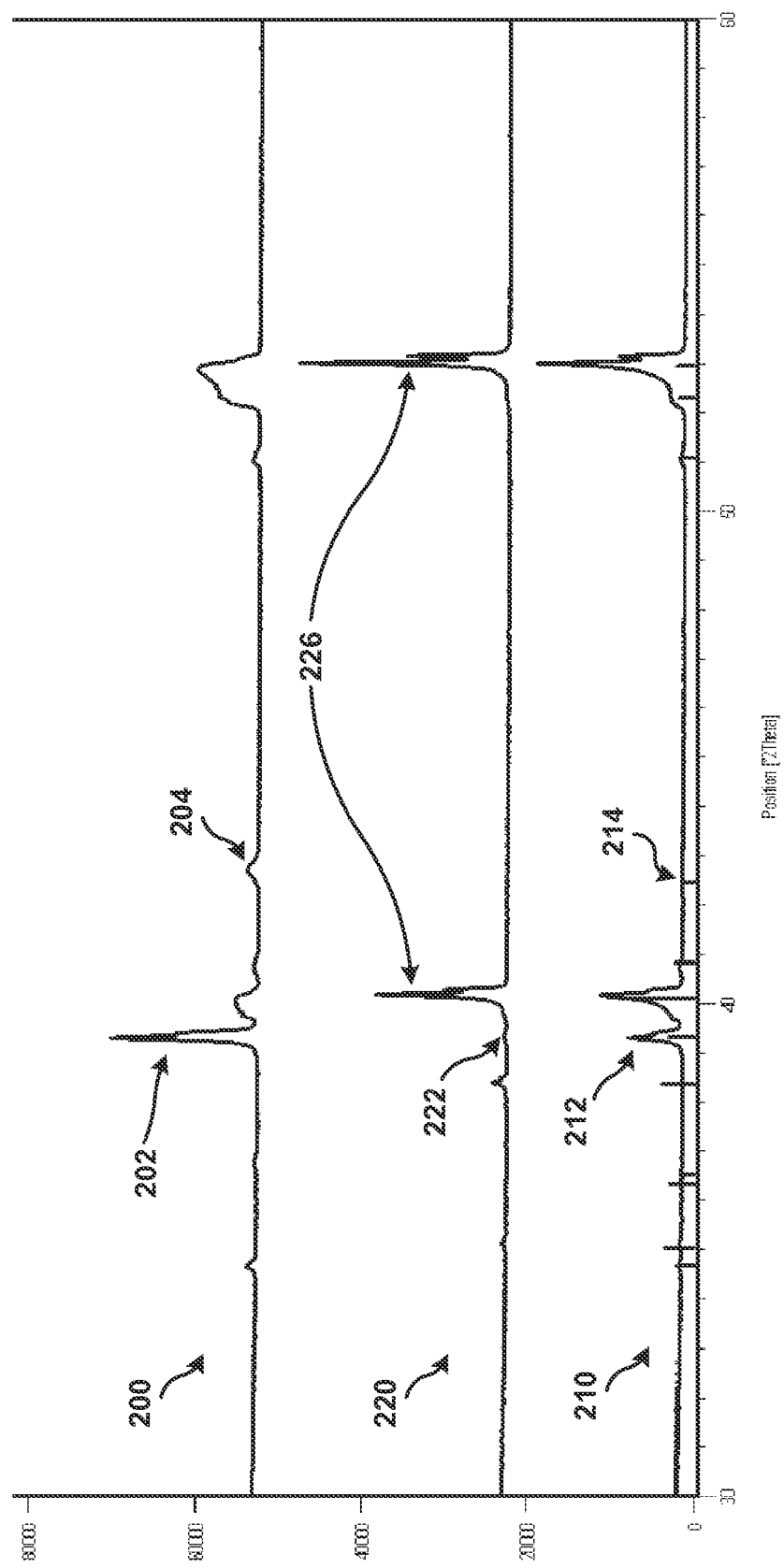
FIG. 11 is an x-ray diffraction graph showing data for sample titanium current collectors of Examples 1, 2, and 4.

Additional samples of current collectors of Examples 1, 2, and 4 were examined by X-ray diffraction (X-pert X-ray diffractometer, Panalytical B. V., Almelo, The Netherlands). Samples of appropriate size were cut from the exemplary current collectors and mounted on quartz zero-background mounts. The test conditions comprised and angular range of 20-130 degrees 2 theta, a 0.02 degree step size, and a 160 second dwell time and rotation. The primary radiation source was filtered copper K-alpha. The resulting X-ray diffraction data of samples of Examples 1, 2, and 4 is shown in FIG. 11, discussed in more detail below.

Scanning Electron Microscopy

Sample current collectors of Examples 1, 2 and 4 were bent approximately 180 degrees to induce surface film fracture and then partially re-straightened. Specimens for scanning electron microscopy were cut from the previously bent regions and examined in a scanning electron microscope (JSM 6301FXV-plus, JEOL Ltd, Tokyo, Japan) at magnifications ranging from a magnification factor of 180 to a magnification factor of 25,000. FIGS. 12A, 12B, 13A, 13B, 14A, and 14B show scanning electron micrographs (SEMs) of sample current collectors of Examples 1, 2, and 4, as described in more detail below.

Corrosion Resistance ("Leaching") Test

Sample titanium current collectors were tested for "leaching" of the underlying titanium bulk. The "leaching" test exposes the current collectors to a chemical solution that is more chemically aggressive than the example fluorine-containing electrolytes described above for use within the example battery cell 66 of battery 62 within the example IMD 16 in order to assess the integrity and corrosion resistance of the surfaces of the current collectors. The test comprises immersing the sample current collector in a solution of 12% $HNO_3$+0.25% HF for about 40 minutes and analyzing the resulting solution via inductively coupled plasma optical emission spectroscopy (ICP-OES) to determine the titanium concentration in the solution. For the case of a theoretically perfect protective coating, the concentration of titanium in the solution would be substantially equal to zero, so a lower value for the titanium concentration corresponds to better corrosion resistance. Resulting data for the leaching test for samples of Examples 1, 2, 3, and Comparative Examples 5 and 6 is shown in Tables 1 and 2, discussed in more detail below.

Accelerated Electrical Testing of Example Batteries

Figure 15:
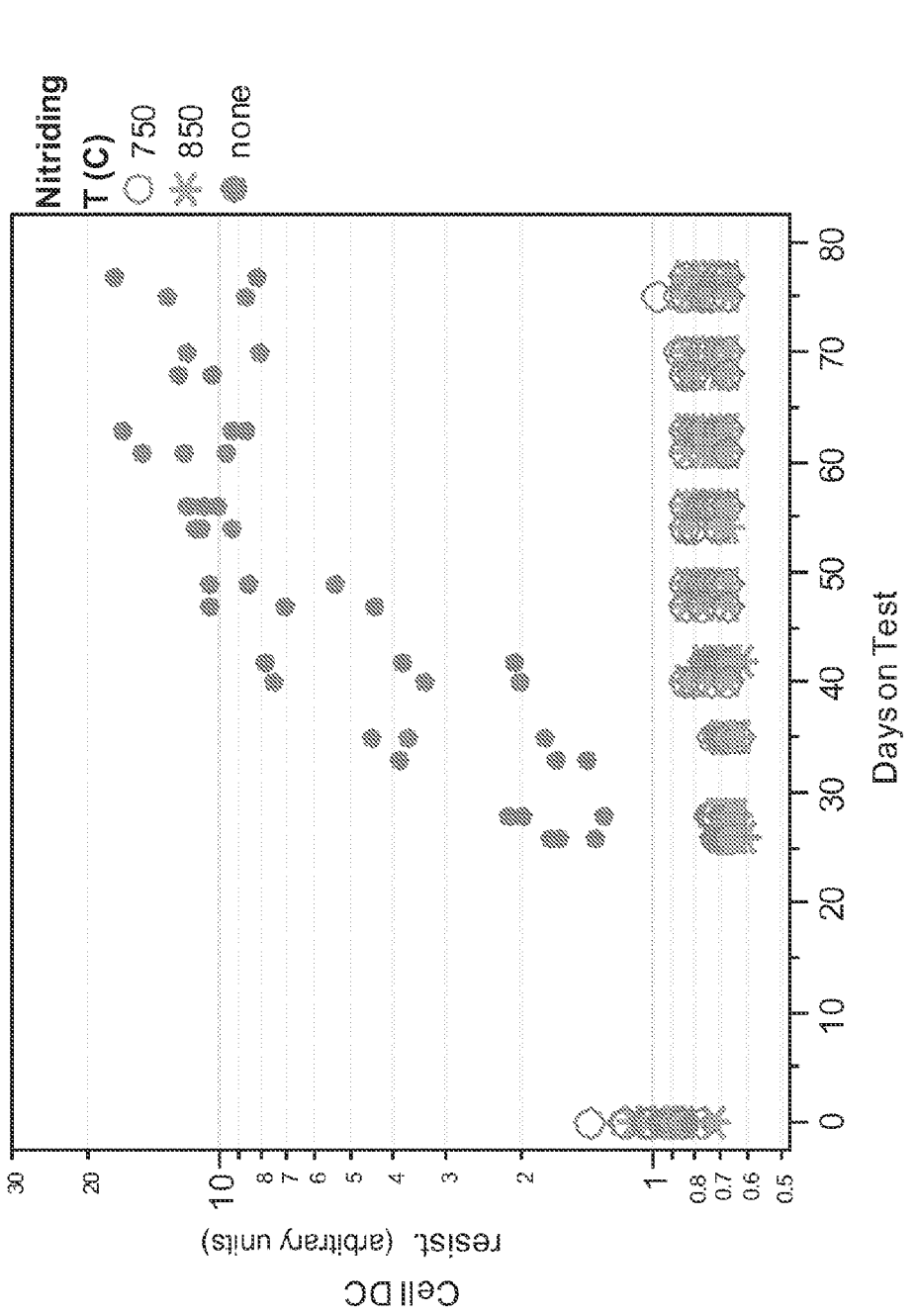
FIG. 15 shows data from an accelerated electrical test of batteries including sample current collectors of Examples 1, 2, and Comparative Example 6.

Further samples of current collectors of Examples 1 and 2 and the untreated Comparative Example 6 were built into complete, hermetically-sealed, high-power test battery cells comprising an internal structure similar to electrode assembly 86 described above with respect to FIG. 6. The test battery cells are electrically tested at elevated temperatures for a period of 77 days (11 weeks). The elevated temperatures greatly accelerate degradation of electrical contact between a cathode current collector and adjacent cathode material such that the 77 days of the test may simulate the passage of "real time" for an IMD implanted in a patient that exceeds the estimated device lifetime. The cells are loaded with a high value resistor for the duration of the test. Periodically, a current sink is used to apply an additional load to each sample cell. The difference between the cell voltages measured with the high resistance load and current-sink load is used to calculate the DC cell resistance using Ohm's law. Low values of DC cell resistance for the Accelerated Electrical Test indicates less corrosion on the current collector and thus less degradation of electrical contact between the current collector and the cathode material. Conversely, high DC cell resistance values, and in particular increasing DC cell resistances over time, indicate the formation of corrosion and the degradation of electrical contact. The resulting data of the accelerated electrical test for Examples 1 and 2 and Comparative Example 6 are shown in FIG. 15, discussed in more detail below.

Example 1

Samples current collectors were placed in a furnace boat comprising titanium foil and placed in the hot zone of a quartz-tube vacuum furnace. (RED MINI furnace, R.D. Webb Co., Natick, Mass.). The furnace was evacuated to an absolute pressure of less than about 0.013 Pa (about $1 \times 10^{-4}$ Torr) using a turbomolecular pump (Model 8722-23-941, BOC Edwards, Crawley, UK) for about 1 hour. The furnace was then ramped up to a furnace soak temperature of about 850° C. at a rate of about 20° C. per minute. When the furnace temperature was at about 450° C., the turbomolecular pump power was turned off and a nitrogen flow of about 0.23 standard cubic meters per minute (about 8 standard cubic feet per minute) was initiated, which resulted in an $N_2$ partial pressure in the furnace of about 4 kPa (about 30 Torr). The furnace was held at the 850° C. soak temperature for about 2 hours and then allowed to cool while maintaining the $N_2$ flow and partial pressure. After the furnace temperature decreased to less than about 50° C., the furnace was vented to the atmosphere and the sample current collectors were removed.

Example 2

Sample current collectors were prepared as described above in Example 1, except that a furnace soak temperature of about 750° C. was used.

Example 3

Sample current collectors were prepared as described above in Example 1, except that a furnace soak temperature of about 675° C. was used.

Example 4

Sample current collectors were prepared as described above in Example 1, except that a furnace soak temperature of about 650° C. was used.

Comparative Example 5

A sample current collector was coated with a TiN coating formed by cathodic arc physical vapor deposition (CAPVD).

Comparative Example 6

Sample current collectors in their "as received" condition from the supplier were used as controls for comparison with thermally nitrided examples in the corrosion resistance (leaching) tests and accelerated electrical tests.

Results

FIG. 11 shows x-ray diffraction data for sample current collectors. FIG. 11 includes an x-ray diffraction data graph 200 for a sample current collector according to Example 1 (e.g., processing temperature of 850° C.), an x-ray diffraction data graph 210 for a sample current collector according to Example 2 (e.g., processing temperature of 750° C.), and an x-ray diffraction data graph 220 for a sample current collector according to Example 4 (e.g., processing temperature of 650° C.). As shown in FIG. 11, the sample current collector of Example 1 shows a relatively large peak 202 indicating a relatively thick $Ti_2N$ inner layer, similar to inner layer 106 shown in FIG. 7, and a smaller peak 204 indicating a thin TiN outer layer, similar to outer layer 108 shown in FIG. 7. FIG. 11 also indicates that the current collector of Example 2 shows a smaller peak 212 indicating a $Ti_2N$ layer that is thinner than the $Ti_2N$ layer of the current collector of Example 1. There is also a small, nearly undetectable rise 214 indicating a very thin TiN layer that is thinner than the TiN layer of the current collector of Example 1 (FIG. 11A). As is further shown in FIG. 11, the current collector of Example 4 shows a small peak 222 indicating a very thin $Ti_2N$ layer and no detectable peak associated with TiN, indicating that a TiN layer may not be formed. FIG. 11 further shows two peaks 226 associated with titanium, indicating that the remainder volume sampled by the x-ray diffraction method comprises Ti. The narrow width of peaks 226 in diffraction data graph 220 indicate the presence of less dissolved nitrogen in the titanium bulk of the current collector than diffraction data graphs 200 and 210, wherein the corresponding peaks are broader.

The x-ray diffraction data of FIG. 11 indicates that an increase in the thickness of a $Ti_2N$ layer formed and an emergence of a TiN layer and an increase in the thickness of the TiN layer results as the processing (soak) temperature of the thermal nitriding process is increased. For example, at a soak temperature of about 650° C., no TiN is detected and only a very thin $Ti_2N$ layer is observed. When the temperature is raised to 750° C., a very thin TiN layer is observed and a thicker $Ti_2N$ layer is formed. Finally, when the temperature is raised to 850° C., an even thicker TiN layer and $Ti_2N$ layer is formed.

Figure 12A:
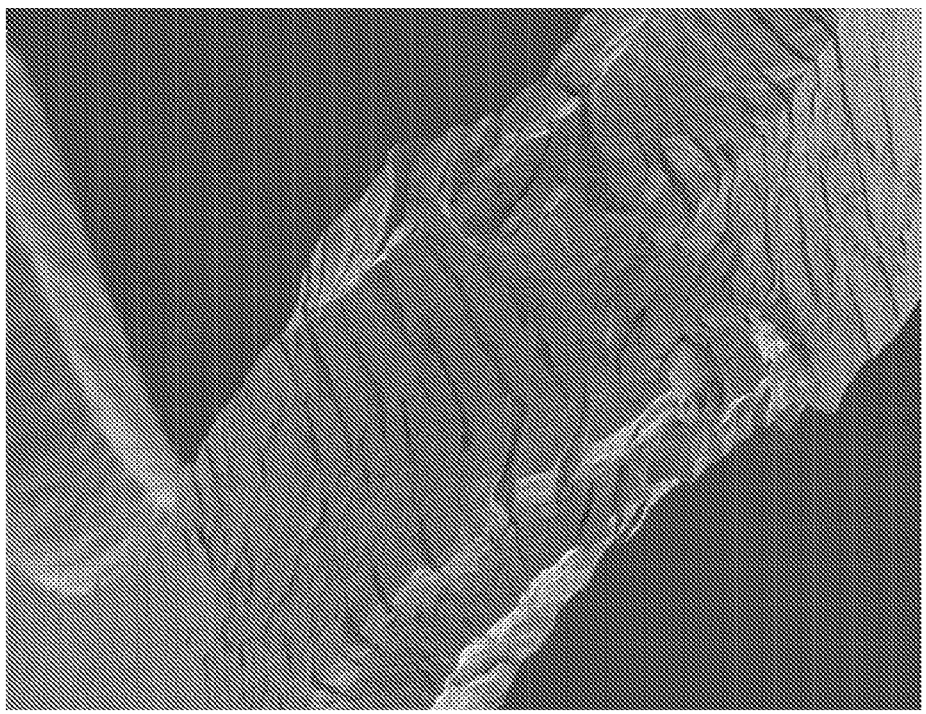
FIGS. 12A, 12B, 13A, 13B, 14A, and 14B are images from a scanning electron microscope showing corrosion-resistant surface regions of increased nitrogen concentration formed on sample titanium current collectors of Examples 1, 2, and 4 at different magnification levels.
Figure 12B:
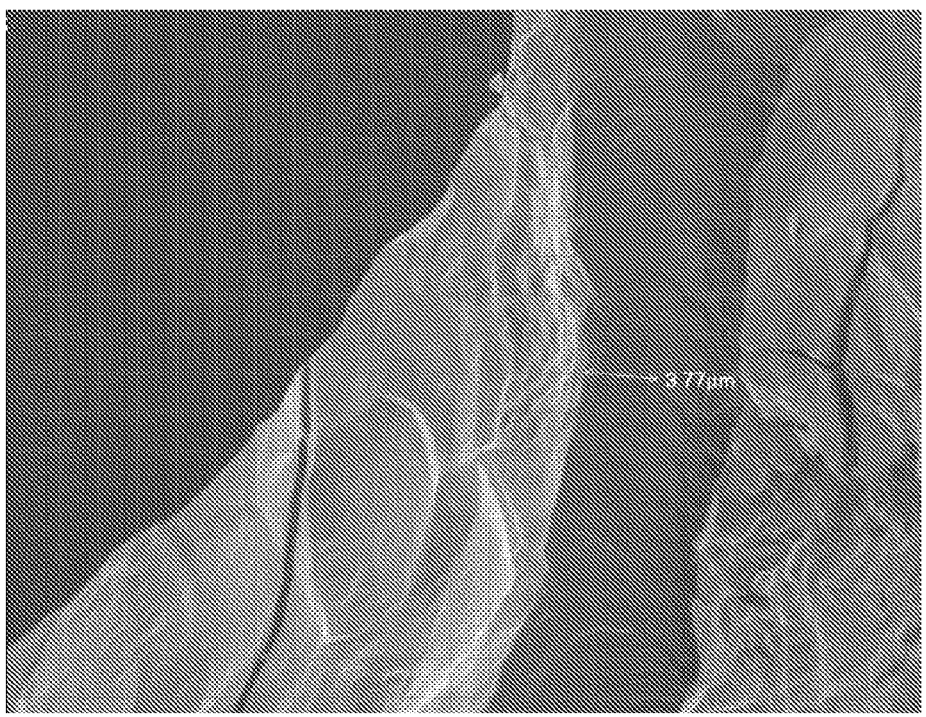
Figure 13A:
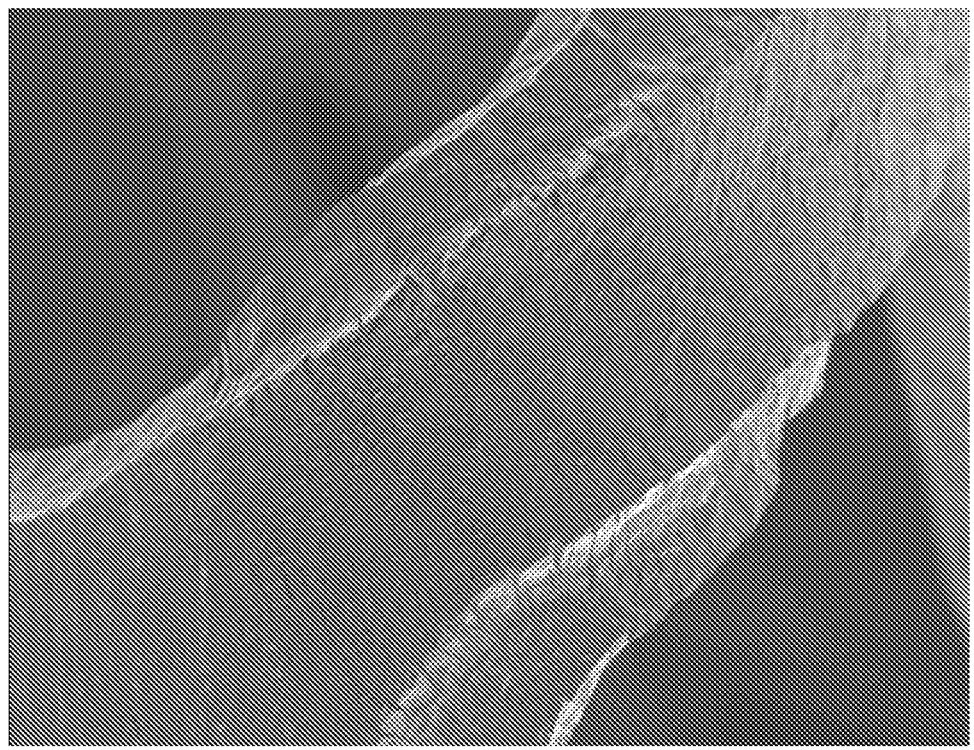
Figure 13B:
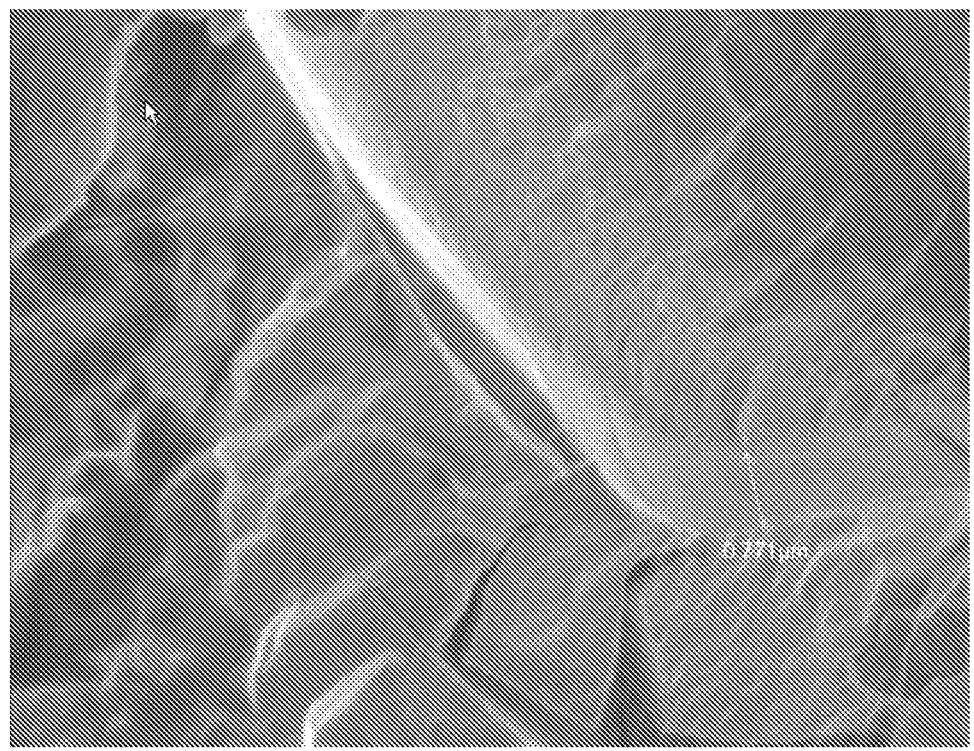
Figure 14A:
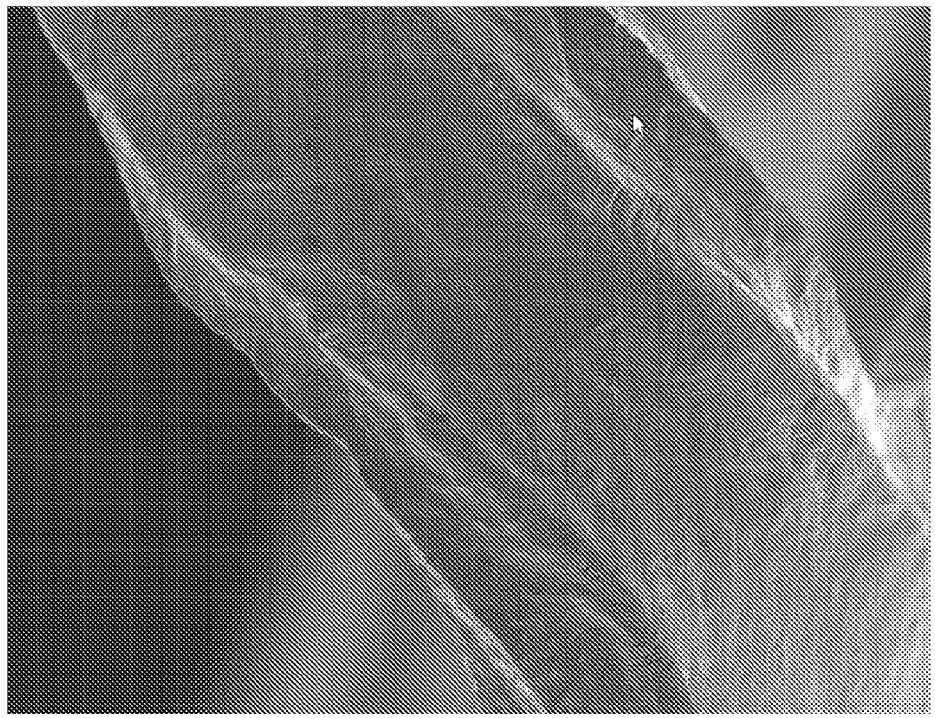
Figure 14B:
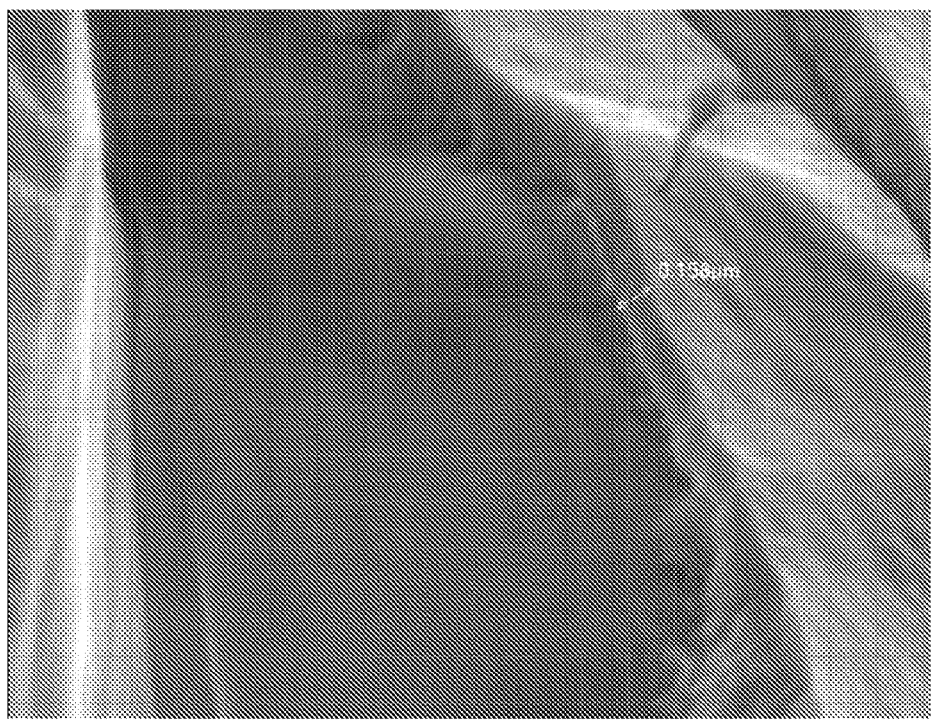

FIGS. 12A, 12B, 13A, 13B, 14A, and 14B show scanning electron micrographs (SEMs) taken of the resulting corrosion-resistant surface regions of increased nitrogen concentration for the sample current collectors made by the methods of Examples 1, 2, and 4. FIG. 12A is a low magnification overview (e.g., taken at 180 times magnification) of a sample current collector made according to Example 1 (e.g., a current collector thermally nitrided at a soak temperature of about 850° C.). FIG. 12A shows a general morphology of surface cracking in a bend region of the sample current collector of Example 1. FIG. 12B shows the sample current collector of Example 1 at a larger magnification of 2000 to enable an approximate measurement of the thickness $T_{Film}$ described with respect to FIG. 7. FIGS. 13A and 13B are an analogous pair of SEMs for a sample current collector of Example 2 (e.g., a current collector thermally nitrided at a soak temperature of about 750° C.). FIG. 13A shows a low-magnification view (at a magnification of 200) and FIG. 13B shows a high-magnification view (at a magnification of 10,000) of the current collector of Example 2. FIGS. 14A and 14B are an analogous pair of SEMS for a sample current collector of Example 4 (e.g., a current collector thermally nitrided at a soak temperature of about 650° C.). FIG. 14A shows a low-magnification view (at a magnification of 200) and FIG. 14B shows a high-magnification view (at a magnification of 25,000) of the current collector of Example 4.

Comparison of the low-magnification views of FIGS. 12A, 13A, and 14A reveals that cracking severity decreases as the thermal nitriding process temperature decreases. Comparison of the high-magnification views of FIGS. 12B, 13B, and 14B indicate that the film thickness $T_{Film}$ decreases from about 3.8 micrometers for the 850° C. process temperature of Example 1, to about 0.77 micrometers for the 750° C. process temperature of Example 2, to about 0.16 micrometers for the 650° C. process temperature of Example 4. Inspection of FIG. 12A shows that even for the case of the highest Example 1 process temperature where both $T_{Film}$ and nitrogen penetration into the underlying alpha titanium are greatest and cracking is most severe, the film exhibits significant ductility and for the most part adheres completely to the current collector. Although some of the corrosion-resistant film is bowing away from the titanium underneath, the remainder of the corrosion-resistant film remains strongly bonded to the titanium. So long as a substantial portion of current collector remains covered and bonded to the corrosion-resistant film, the current collector will not undergo significant corrosion and/or degradation by the electrolyte compounds of the battery, and good electrical contact between the current collector and cathode material will be maintained, and the battery impedance will desirably remain stable.

Table 1 provides a summary of results of the corrosion resistance ("leaching") test for sample current collectors treated by the methods of Examples 1-3 and comparable current collectors that are untreated (Comparative Example 6).

TABLE 1

| Example No. | Thermal Nitriding Soak Temperature (° C.) | Dissolved Ti (µg/mL) |
|---|---|---|
| 1 | 850 | <10 |
| 1 | 850 | 28.8 |
| 2 | 750 | 37.4 |
| 2 | 750 | 109 |
| 3 | 675 | 809 |
| 3 | 675 | 1290 |

TABLE 1-continued

| Example No. | Thermal Nitriding Soak Temperature (° C.) | Dissolved Ti (µg/mL) |
|---|---|---|
| Comp. 6 | N/A | 2740 |
| Comp. 6 | N/A | 2720 |

The results of the corrosion resistance test shown in Table 1 indicates that corrosion protection increases with increasing process temperature, however, even the lowest process temperature (675° C.) with the smallest $T_{Film}$ (as extrapolated from the SEM in FIG. 14B of the current collector of Example 4 (processing temperature of 650° C. rather than 675° C. as in Example 3) exhibits leaching solution titanium concentrations two to three times lower than is observed for the untreated current collector of Comparative Example 6.

Table 2 provides a summary of results of the corrosion resistance ("leaching") test for sample current collectors similar to the perforated sheet current collector 80 shown in FIG. 4. Samples of the perforated sheet current collectors 80 were treated by thermal nitriding as described above in Examples 1, 2, and 4, as well as via CAPVD as in Comparative Example 5.

TABLE 2

| Example No. | Thermal Nitriding Soak Temperature (° C.) | Dissolved Ti (µg/mL) |
|---|---|---|
| 1 | 850 | <10 |
| 1 | 850 | <10 |
| 2 | 750 | 60.7 |
| 2 | 750 | 108 |
| 4 | 650 | 244 |
| 4 | 650 | 344 |
| Comp. 5 | N/A | 50 |
| Comp. 5 | N/A | 500 |

The results of the corrosion resistance test shown in Table 2 indicates that the corrosion-resistant surface regions formed by the thermal nitriding process of Examples 1, 2, and 4 provide for corrosion protection that is at least comparable to corrosion protection that is provided by a TiN coating deposited by CAPVD.

FIG. 15 shows accelerated electrical test data in the form of DC cell resistance over time for the thermally nitrided current collectors of Examples 1, 2, and for an untreated current collector of Comparative Example 6. As shown in FIG. 15, the DC cell resistance remains desirably low and stable for the duration of the test for the current collectors of Example 1 and Example 2, for substantially the entire duration of the test (77 days). The untreated current collector of Comparative Example 6 exhibited a generally exponential increase in DC cell resistance up to an apparent maximum that may be more than 10 times greater than exhibited by the cells comprising the Example 1 and 2 current collectors. The data corresponding to Comparative Example 6 (untreated current collector) indicates an unstable resistance that is may be unacceptably high and unstable resistance.

Various examples have been described. These and other examples are within the scope of the following claims.

The invention claimed is:

1. A method comprising:
    baking a component of an implantable medical device, the component comprising at least one of titanium, a titanium-based alloy, or composites thereof; and
    simultaneously exposing the component to a nitrogen-bearing gas so that a corrosion-resistant surface region forms at an exposed surface of the component, the corrosion-resistant surface region comprising at least one of titanium nitride, dititanium nitride, and a solid solution of nitrogen dissolved in the component, wherein the component forms a current collector for a battery of the implantable medical device.

2. The method of claim 1, wherein baking the component comprises baking the component at a temperature of between about 600° C. and about 880° C.

3. The method of claim 1, wherein baking the component comprises baking the component at a temperature of between about 650° C. and about 750° C.

4. The method of claim 1, wherein the nitrogen-bearing gas has a partial pressure of at least 5 pascals (about 0.04 torr) or greater.

5. The method of claim 1, wherein the component is baked within a furnace, further comprising creating a vacuum in the furnace after placing the component in the furnace in order to evacuate air from the furnace.

6. The method of claim 5, wherein creating the vacuum comprises evacuating the furnace to an absolute pressure of between about 0.005 pascal (about $3.75 \times 10^{-5}$ torr) and about 0.025 pascal (about $1.88 \times 10^{-4}$ torr).

7. The method of claim 5, wherein baking the component comprises increasing the temperature within the furnace after creating the vacuum.

8. The method of claim 7, wherein exposing the component to the nitrogen-bearing gas comprises feeding a flow of nitrogen gas to the furnace until a nitrogen partial pressure of at least 5 pascals or greater is achieved.

9. The method of claim 8, wherein the flow of nitrogen-bearing gas is between about 0.001 standard cubic meters per minute (about 0.035 standard cubic feet per minute) of nitrogen gas and about 0.3 standard cubic meters per minute (about 10.6 standard cubic feet per minute) of nitrogen gas.

10. The method of claim 8, wherein the flow of nitrogen gas is initiated when the temperature within the furnace has reached between about 300° C. and about 600° C.

11. The method of claim 1, wherein baking the component comprises baking the component at a temperature of between about 600° C. and about 880° C. for between about 1.5 hours and about 3 hours.

12. The method of claim 1, wherein the partial pressure of the nitrogen-bearing gas while exposing the component to the nitrogen-bearing gas is about 4 kilopascals (about 30 torr).

13. The method of claim 1, further comprising allowing the component to cool while continuing to expose the component to nitrogen gas.

14. The method of claim 1, wherein the component consists essentially of a commercially pure grade of titanium.

15. The method of claim 1, wherein the current collector comprises a complex geometry.

16. The method of claim 1, wherein the corrosion-resistant film is inert to a fluorine-containing compound.

17. The method of claim 1, wherein the fluorine-containing compound comprises a fluorine-containing electrolyte for an electrochemical battery cell of the implantable medical device.

18. A method comprising:
baking a component of an implantable medical device, the component comprising at least one of titanium, a titanium-based alloy, or composites thereof; and
simultaneously exposing the component to a nitrogen-bearing gas so that a corrosion-resistant surface region forms at an exposed surface of the component, the corrosion-resistant surface region comprising at least one of titanium nitride, dititanium nitride, and a solid solution of nitrogen dissolved in the component, wherein the component forms a current collector for a battery of the implantable medical device and wherein the implantable medical device delivers a therapy comprising at least one of cardiac rhythm management, pacing pulses, cardioversion shocks, and defibrillation shocks.

19. A method comprising:
baking a component of an implantable medical device, the component comprising at least one of titanium, a titanium-based alloy, or composites thereof; and
simultaneously exposing the component to a nitrogen-bearing gas so that a corrosion-resistant surface region forms at an exposed surface of the component, the corrosion-resistant surface region comprising at least one of titanium nitride, dititanium nitride, and a solid solution of nitrogen dissolved in the component, wherein the component comprises a perforated sheet.

* * * * *